United States Patent
Goettel et al.

(12) 
(10) Patent No.: US 6,312,478 B1
(45) Date of Patent: Nov. 6, 2001

(54) COLORANT AND METHOD FOR PRODUCING TEMPORARY HAIR COLORS

(75) Inventors: Otto Goettel, Marly; Aline Pirrello, Givisiez, both of (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/403,818

(22) PCT Filed: Feb. 26, 1999

(86) PCT No.: PCT/EP99/01235

§ 371 Date: Oct. 26, 1999

§ 102(e) Date: Oct. 26, 1999

(87) PCT Pub. No.: WO99/44569

PCT Pub. Date: Sep. 10, 1999

(30) Foreign Application Priority Data

Mar. 6, 1998 (DE) .............................................. 198 09 646

(51) Int. Cl.$^7$ ...................................................... A61K 7/13
(52) U.S. Cl. .................. 8/405; 8/423; 8/568; 8/571; 8/102; 8/431; 8/548; 548/366.1
(58) Field of Search ............................... 8/405, 423, 568, 8/571, 573, 102, 431; 548/366.1

(56) References Cited

U.S. PATENT DOCUMENTS

| | | | |
|---|---|---|---|
| 3,681,345 | * 8/1972 | Bland | 544/300 |
| 4,218,432 | * 8/1980 | Watanabe et al. | 548/366.1 |
| 4,266,014 | * 5/1981 | Moelants et al. | 548/366.1 |
| 4,288,534 | * 9/1981 | Lemahieu et al. | 548/366.1 |
| 4,440,852 | * 4/1984 | Onishi et al. | 548/366.1 |
| 4,681,471 | 7/1987 | Hayduchok et al. | 401/34 |
| 5,013,636 | * 5/1991 | Ohno et al. | 430/522 |

FOREIGN PATENT DOCUMENTS

| | | |
|---|---|---|
| 38 42 774 C1 | 3/1990 | (DE). |
| 196 18 595 A1 | 11/1997 | (DE). |

OTHER PUBLICATIONS

Houben–Weyl 5/1D, 4. Auflage, Berlin et al., pp. 296–299, 1954.
B. Scheid: "Umsetzungen Von Formamid Mit Carbonyl-verbindungen", J. Prakt. Chem 157, pp. 203–224, 1941 (no month available).
S. Huenig: "Ueber Die Bildung Von Methinbruecken . . . ", Annalen 574, PP 106–121., 1951 (no month available).

* cited by examiner

*Primary Examiner*—Margaret Einsmann
(74) *Attorney, Agent, or Firm*—Michael J. Striker

(57) ABSTRACT

The method for temporarily coloring and later decolorizing hair includes applying a colorant to the hair, which contains a monomethine or polymethine dye of formula (Ia/Ib), or a salt thereof, $$W=L-V' \text{ (Ia)} \leftrightarrows W'-L=V \text{ (Ib)},$$

wherein W=L–V' and W'=L–V are tautomers, W and V are each a substituted five-member or six-member heterocyclic ring, each of which is a substituted pyrazolone, substituted pyridone, substituted dioxothiazoline, substituted rhodanine, substituted dioxoimidazolidine or substituted barbituric acid;

wherein L represents $-[-CH=CH-]_m-CR=[=CH-CH=]_n-$ and R is hydrogen, a phenyl group, a halogen atom, a methyl group or a carboxamido group, and wherein m and n are each 0, 1 or 2, but $n+m \leq 2$; then allowing the colorant to act for from 10 to 45 min at 20 to 50° C.; subsequently rinsing with water and drying and at a later time, decolorizing the hair with a reducing agent or an oxidant.

47 Claims, No Drawings

COLORANT AND METHOD FOR PRODUCING TEMPORARY HAIR COLORS

BACKGROUND OF THE INVENTION

1. Field of the Invention

The present invention relates to nonoxidative hair colorants based on certain anionic polymethine dyes and to a method for temporary hair coloration whereby the coloration can be removed at any time.

The coloring of hair is currently subject to the most varied trends. Whereas in the past hair was colored primarily to cover gray areas, today there is an increasing demand for integrating the hair color into current fashion as an expression of personality.

Now as before, two established methods of hair coloring are available. One of these is the oxidative hair coloring which a priori is unsuitable for temporary coloring, because it produces a very durable coloring result. The other method consists of the possibility of coloring hair with colorants containing nonoxidative, direct dyes (often referred to as toners). Although the dyes used for this purpose are optimized for dyeing performance as well as for remaining on the hair as long as possible, the color shade gradually fades with every hair washing. Thus, depending on the product used and the type of hair, such colorations as a rule do not last more than a maximum of 10 hair washings. If the user of such nonoxidative colorants would like to restore her original hair color at an earlier time, no satisfactory means are currently available for rapidly restoring the original color, because the products used for this purpose are usually very aggressive causing hair damage.

2. Prior Art

In the literature are described many attempts to restore the color of fibers. For example, German Patent DE 38 42 74 and U.S. Pat. No. 4,681,471 describe the decoloration of triarylmethane dyes with reducing agents. U.S. Pat. No. 5,474,578 uses the same approach based on the use of oxidative or reductive decoloration or a combination of these two treatments. A general problem underlying these methods is, in particular, that in most cases only partial decoloration is attained. Thus the method of U.S. Pat. No. 5,474,578 in the most favorable case produces a maximum degree of decoloration of 90 to 93%, and this degree of decoloration can be achieved only by applying a reductive treatment after an oxidative one. Such double treatment, however, causes extraordinary hair damage. Normally, such a method produces only partial (often <50%) hair decoloration.

The foregoing patents also have in common that they deal with the decoloration of dye classes that have been used in hair cosmetics for a long time. The colorants are based on direct dyes with different chemical and physical properties and with different coloring and bleaching characteristics. Hence, at least for color shading that requires dye mixtures, it is very difficult to produce uniform decoloration, because the result is determined by the properties of the least active component.

Hence, a need exists for nonoxidative colorants that can be removed at any time without causing major hair damage.

Some of the polymethine dyes and their suitability for the coloring of fibers have been known for a long time. A review of these dyes can be found, for example, in Houben-Weyl 5/1d, 4th edition (1954) page 227 ff. Some of these polymethine dyes are also commercially available. Although in some cases good to satisfactory coloring results are obtained, a complete removal of such dyes is usually very difficult. Thus pentamethine isooxazolone dyes produce a coloration, but the removal of this coloration is possible only to an insufficient degree.

SUMMARY OF THE INVENTION

Surprisingly, we have now found that colorants based on certain anionic polymethine dyes (in the following referred to as "oxonol dyes"), particularly the pyrazolone and pyridone compounds of formulas (II) to (IV), produce excellent hair coloration which can again be removed within a short time in simple and gentle manner. The decoloration can be achieved with either reducing or oxidizing agents, the use of reducing decolorizing agents being preferred.

By means of the colorants of the invention, it is possible to achieve color shades of a modified natural tone but particularly those in the fashionable range. Moreover, besides the said color shades it is possible to obtain a number of highlights, particularly in the bright-red to blue range. As a result of the high tinting power of the dyes and their high substantivity, the original fiber color can be covered very effectively. As a result, it is possible to satisfy the aforementioned desire to integrate the hair coloration into fashion and to provide an expression of personality.

Hence, the object of the present application is a hair colorant characterized in that it contains at least one oxonol dye of the tautomeric formula (Ia)/(Ib) or a physiologically tolerated salt thereof,

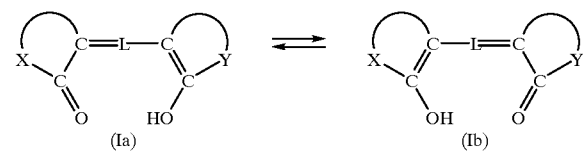

wherein in the general formula (Ia)/(Ib) X and Y independently of each other and always together with the two carbon atoms of the ring system indicated in formula (Ia)/(Ib) represent elements required for the formation of a five-membered or six-membered heterocyclic ring, and L denotes a bridging group of general formula

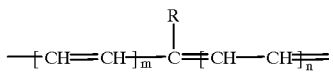

wherein R denotes a hydrogen atom, a phenyl, methyl or carboxamido group or a halogen atom, and the indices m and n each equal 0, 1 or 2, the sum of m and n not exceeding 2.

In general formula (Ia)/(Ib), it is possible to use as the five-membered or six-membered heterocyclic ring a pyrazolone, pyridone, dioxothiazoline, rhodanine, dioxoimidazoline or barbituric acid group, the ring systems in general formula (Ia)/(Ib) being either equal or different. Preferably, these two ring systems are equal keeping in mind that they are tautomeric forms, and L stands for a monomethine unit, trimethine unit or pentamethine unit.

Physiologically tolerated salts of the compounds of formula (Ia)/(Ib) are, in particular, the alkali metal and ammonium salts, for example the ammonium, sodium, potassium, N-methylmorpholinium, monoethanolammonium, diethanolammonium and triethanolammonium salts, among which the sodium, potassium and particularly ammonium salts are preferred.

When represented in their acid form, the dyes of the present invention preferably have the structures of general formulas (II) to (IV), shown in one of their possible tautomeric forms

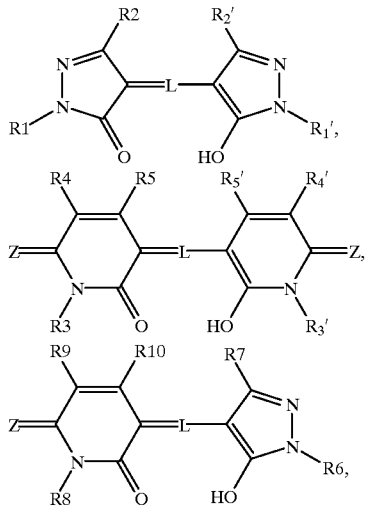

wherein R1, R1' and R6 denote hydrogen, a straight-chain or branched C1 to C8 alkyl, hydroxyethyl, dihydroxypropyl, methoxyethyl, carboxyethyl or C1 to C4 sulfoalkyl group, or a phenyl group possibly substituted with one or more halogen atoms, one or two sulfonic acid groups, one or two carboxyl groups, one or more unbranched or branched C1 to C8 alkyl groups or C1 to C8 alkoxy groups, or a benzyl group possibly substituted with one or more halogen atoms, a C1 to C4 alkyl, hydroxyl, methoxy, carboxyl, nitro or amino group or a five-membered or six-membered saturated or unsaturated heterocyclic ring, R1 and R1' being equal or different, and R2, R2' and R7 denote hydrogen, a branched or unbranched C1 to C6 alkyl, phenyl or amino group which can also be acylated or sulfonylated, an acetyl, methoxy or carboxyl group possibly esterified with a straight-chain or branched C1 to C8 alcohol or ethylene glycol monomethyl ether or ethylene glycol monoethyl ether, a carboxamido, carboxanilido, 2-amino-2-oxyethyl or nitrilo group, R2 and R2' being equal or different, and R3, R3' and R8 denote hydrogen, a straight-chain or branched C1 to C11 alkyl group, a straight-chain or branched C1 to C11 monohydroxyalkyl group, a straight-chain or branched C1 to C11 dihydroxyalkyl group, a straight-chain or branched C1 to C11 alkoxyalkyl group, a straight-chain or branched C1 to C11 monoalkylamino group, a straight-chain or branched amino group of formula $(CH_2)_x$—NR11R12 (where x is an integer from 0 to 3 and R11 and R12 independently of each other denote a C1 to C3 alkyl group), a C2 to C4 sulfoalkyl or group, carboxyalkyl group or a phenyl group possibly substituted with one or more halogen atoms, one or two sulfonic acid groups, one or two carboxyl groups, one or more unbranched or branched C1 to C8 alkyl groups or C1 to C8 alkoxy groups, or a benzyl group possibly substituted with one or more halogen atoms, a C1 to C4 alkyl group, a hydroxyl, methoxy, nitro or amino group, a phenylethyl group, a five-membered or six-membered aromatic or nonaromatic heterocyclic ring attached directly or through a methylene group, a pyrrolidino, morpholino, piperazino, piperidino, pyridino(C2 or C3)alkyl or trialkylammoniumalkyl group of formula $R13-N(R14)_3^+$ (where R13 denotes a C1 to C6 alkylene group and R14 denotes a methyl or ethyl group, the total number of carbon atoms in the molecule being equal to 5 to 9) and R3 and R3' being equal or different, and R4, R4' and R9 denote hydrogen, a nitrilo, carboxylate ester, carboxamido, sulfonic acid, sulfomethyl, methanesulfonyl, pyridinium or imidazolium group, R4 and R4' being equal or different, and R5, R5' and R10 denote hydrogen, a C1 to C4 alkyl group, a C5 to C6 cycloalkyl group, a phenyl, methoxyphenyl, benzyl, phenylethyl or carboxyl group, R5 and R5' being equal or different, and Z denotes oxygen or a group of formula $C(CN)_2$, $C(CN)COOQ$ or $C(COOQ)_2$, wherein Q denotes a C1 to C8 alkyl group or an ethylene glycol mono(C3 to C7)alkyl ether, and L stands for a bridging group of general formula

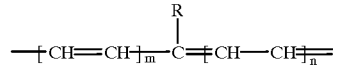

wherein R denotes a hydrogen atom, a phenyl, methyl or carboxamido group or a halogen atom, and the indices m and n each equal 0, 1 or 2, the sum of m and n not exceeding 2.

Particularly preferred are dyes of general formulas (II) to (IV) and salts thereof wherein R1 and R1' are equal and denote hydrogen, a straight-chain or branched C1 to C4 alkyl, hydroxyethyl, dihydroxypropyl, methoxyethyl or C2 to C4 sulfoalkyl group or a phenyl group possibly substituted with one or more halogen atoms, one or two sulfonic acid groups, a methyl or methoxy group, or a benzyl group possibly substituted with a halogen atom or a methyl, hydroxyl, methoxy, nitro or amino group, and R2 and R2' are equal and denote a methyl group or an amino group which can also be acylated, or a carboxyl group possibly esterified with a C1 to C3 alcohol, and R3 and R3' are equal or different and denote hydrogen, a straight-chain C1 to C4 alkyl, hydroxyethyl, methoxyethyl, methoxypropyl or sulfoethyl group or a phenyl group possibly substituted with a halogen atom, a sulfonic acid, methyl or methoxy group, or a benzyl group possibly substituted with a halogen atom or a methyl, hydroxyl, methoxy, nitro or amino group, or a five-membered or six-membered aromatic or nonaromatic heterocyclic ring attached directly or through a methylene group, or an amino group, a C1 to C4 monoalkylamino group, a dialkylamino group with a total of 2 to 8 carbon atoms in the molecule or a trialkylammoniumalkyl group of formula $R13-N(R14)_3^+$ (where R13 denotes a C1 to C6 alkylene group and R14 denotes a methyl or ethyl group, the total number of carbon atoms in the molecule being equal to 5 to 9), and R4 and R4' are equal and denote hydrogen, a nitrile, carboxamido, sulfonic acid, sulfomethyl, methanesulfonyl, pyridinium or imidazolium group, and R5 and R5' are equal and denote a methyl or nitrile group or a substituted or unsubstituted phenyl group, and R6 denotes hydrogen, a straight-chain or branched C1 to C4 alkyl, hydroxyethyl, dihydroxypropyl, methoxyethyl or C2 to C4 sulfoalkyl group or a phenyl group possibly substituted with one or more halogen atoms, one or more sulfonic acid groups, a methyl or methoxy group, or a benzyl group possibly substituted with a halogen atom or a methyl, hydroxyl, methoxy, nitro or amino group, and R7 denotes a methyl or amino group which can also be acylated, or a carboxyl group possibly esterified with a C1 to C3 alcohol, and R8 denotes hydrogen, a straight-chain C1 to C4 alkyl, hydroxyethyl, methoxyethyl or sulfoethyl group or a phenyl group possibly substituted with a halogen atom or a sulfonic acid, methyl or methoxy group, or a benzyl group possibly substituted with a halogen atom or a methyl, hydroxyl, methoxy, nitro or amino group, or a five-membered or six-membered aromatic or non-aromatic heterocyclic ring attached directly or through a methylene group, furthermore an amino or C1 to C4 monoalkylamino group or a dialkylamino group with a total of 2 to 8 carbon atoms in the molecule, or trialkylammoniumalkyl group of formula $R13-N(R14)_3^+$ (where R13 denotes a C1 to C6 alkylene group and R14 denotes a methyl or ethyl group, the total number of carbon atoms in the molecule being equal to 5 to 9), and R9 denotes hydrogen or a nitrilo, carboxamido, sulfonic acid, sulfomethyl, pyridinium or imidazolium group, and R10 denotes hydrogen or a methyl, nitrilo or substituted or unsubstituted phenyl group, and Z denotes oxygen or a $C(CN)_2$ group, and L represents a bridging group of general formula

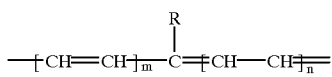

wherein R denotes a hydrogen atom or a methyl group, and the indices m and n each equal 0, 1 or 2, the sum of m and n not exceeding 2.

The following compounds (always shown in one of their possible tautomeric forms) are examples of the aforesaid preferred dyes of formulas (II) to (IV). In their acid form, they can be represented as follows:

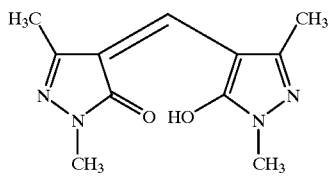

4-(5-Hydroxy-1,3-dimethyl-1H-pyrazol-4-ylmethylen)-2,5-dimethyl-2,4-dihydropyrazol-3-one
(1)

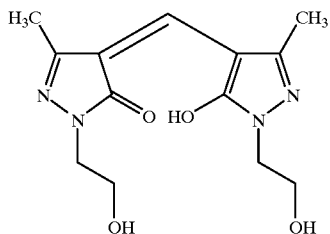

2-(2-Hydroxyethyl)-4-(5-hydroxy-1-(2-hydroxyethyl)-3-methyl-1H-pyrazol-4-ylmethylen)-5-methyl-2,4-dihydropyrazol-3-one (2)

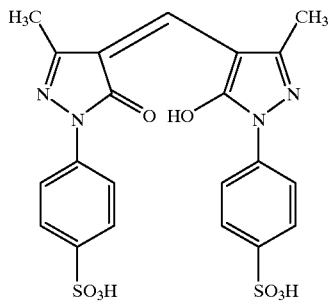

4-(5-Hydroxy-3-methyl-1-(4-sulfophenyl)-1H-pyrazol-4-ylmethylen)-5-methyl-2-(4-sulfophenyl)-2,4-dihydropyrazol-3-one (3)

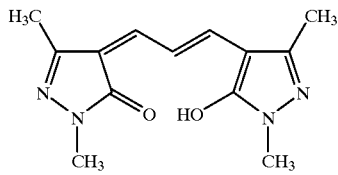

4-(3-(5-Hydroxy-1,3-dimethyl-1H-pyrazol-4-yl)-allyliden)-2,5-dimethyl-2,4-dihydropyrazol-3-one
(4)

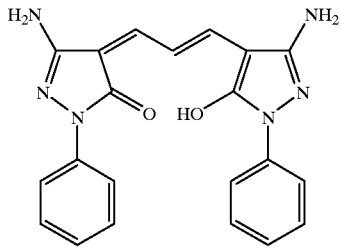

5-Amino-4-(3-(3-amino-5-hydroxy-1-phenyl-1H-pyrazol-4-yl)-allyliden)-2-phenyl-2,4-dihydropyrazol-3-one (5)

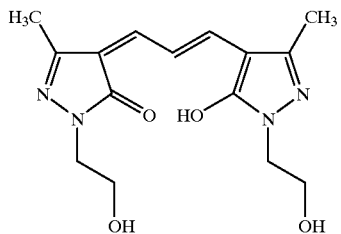

7

2-(2-Hydroxyethyl)-4-(3-(5-hydroxy-1-(2-hydroxyethyl)-3-methyl-1H-pyrazol-4-yl)-allyliden)-5-methyl-2,4-dihydro-pyrazol-3-one (6)

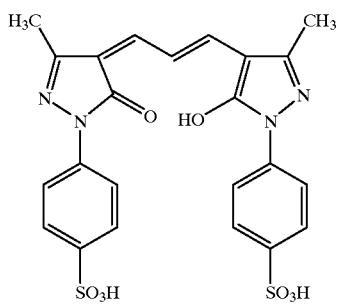

4-(3-(5-Hydroxy-3-methyl-1-(4-sulfophenyl)-1H-pyrazol-4-yl)-allyliden)-5-methyl-2-(4-sulfophenyl)-2,4-dihydro-pyrazol-3-one (7)

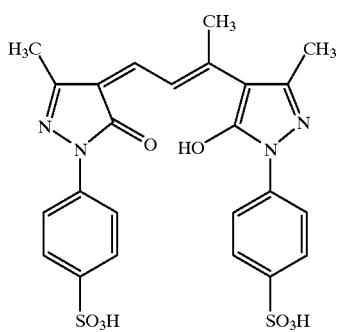

4-(3-(5-Hydroxy-3-methyl-1-(4-sulfophenyl)-1H-pyrazol-4-yl)-but-2-enyliden)-5-methyl-2-(4-sulfophenyl)-2,4-dihydropyrazol-3-one (8)

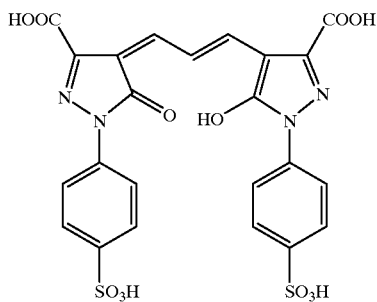

8

4-(3-(3-Carboxy-5-oxo-1-(4-sulfophenyl)-1,5-dihydropyrazol-4-yliden)-propenyl)-5-hydroxy-1-(4-sulfophenyl)-1H-pyrazol-3-carboxylic acid (9)

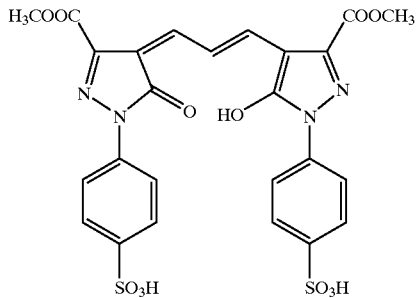

5-Hydroxy-4-(3-(3-methoxycarbonyl-5-oxo-1-(4-sulfophenyl)-1,5-dihydropyrazol-4-yliden)-propenyl)-1-(4-sulfophenyl)-1H-pyrazol-3-carboxylic acid methyl ester (10)

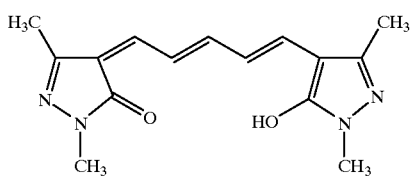

4-(5-(5-Hydroxy-1,3-dimethyl-1H-pyrazol-4-yl)-penta-2,4-dienyliden)-2,5-dimethyl-2,4-dihydropyrazol-3-one (11)

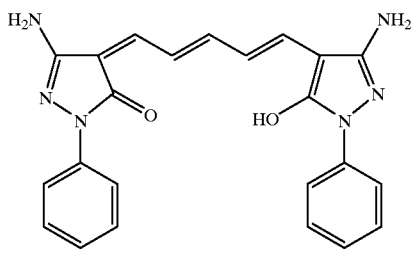

5-Amino-4-(5-(3-amino-5-hydroxy-1-phenyl-1H-pyrazol-4-yl)-penta-2,4-dienyliden)-2-phenyl-2,4-dihydropyrazol-3-one (12)

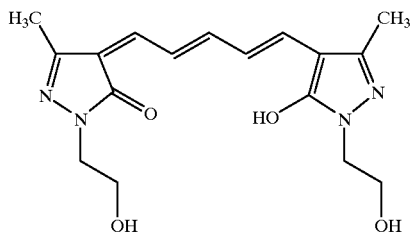

2-(2-Hydroxyethyl)-4-(5-(5-hydroxy-1-(2-hydroxyethyl)-3-methyl-1H-pyrazol-4-yl)-penta-2,4-dienyliden)-5-methyl-2,4-dihydro-pyrazol-3-one (13)

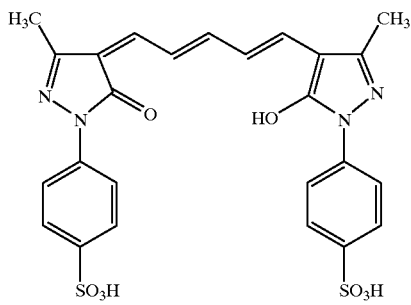

4-(5-(5-Hydroxy-3-methyl-1-(4-sulfophenyl)-1H-pyrazol-4-yl)-penta-2,4-dienyliden)-5-methyl-2-(4-sulfophenyl)-2,4-dihydropyrazol-3-one (14)

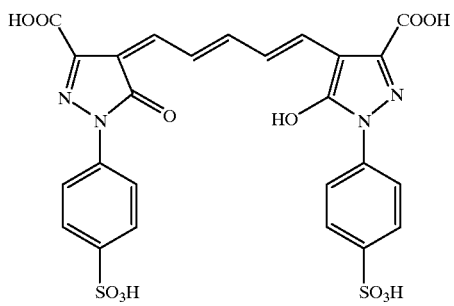

4-(5-(3-Carboxy-5-oxo-1-(4-sulfophenyl)-1,5-dihydropyrazol-4-yliden)-penta-1,3-dienyl)-5-hydroxy-1-(4-sulfophenyl)-1H-pyrazol-3-carboxylic acid (15)

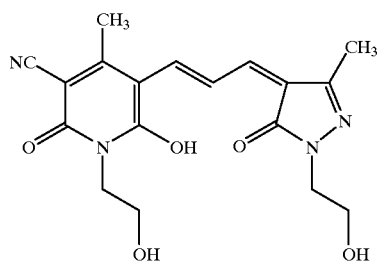

6-Hydroxy-1-(2-hydroxyethyl)-5-(3-(1-(2-hydroxyethyl)-3-methyl-5-oxo-1,5-dihydro-pyrazol-4-yliden)-propenyl)-4-methyl-2-oxo-1,2-dihydro-pyridin-3-carbonitril (16)

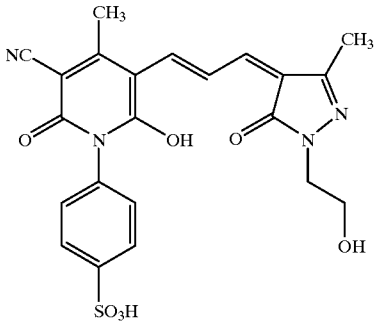

6-Hydroxy-5-(3-(1-(2-hydroxyethyl)-3-methyl-5-oxo-1,5-dihydro-pyrazol-4-yliden)-propenyl)-4-methyl-2-oxo-1-(4-sulfophenyl)-1,2-dihydro-pyridin-3-carbonitril (17)

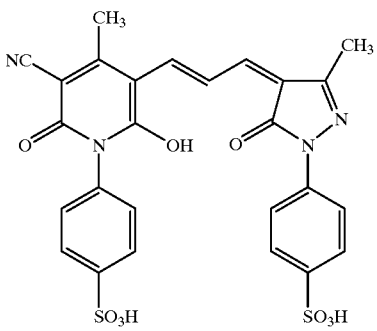

6-Hydroxy-4-methyl-5-(3-(3-methyl-5-oxo-1-(4-sulfophenyl)-1,5-dihydro-pyrazol-4-yliden)-propenyl)-2-oxo-1-(4-sulfophenyl)-1,2-dihydropyridin-3-carbonitril (18)

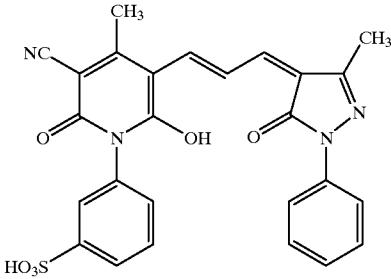

11

6-Hydroxy-4-methyl-5-(3-(3-methyl-5-oxo-1-phenyl-1,5-dihydropyrazol-4-yliden)-propenyl)-2-oxo-1-(3-sulfophenyl)-1,2-dihydropyridin-3-carbonitril (19)

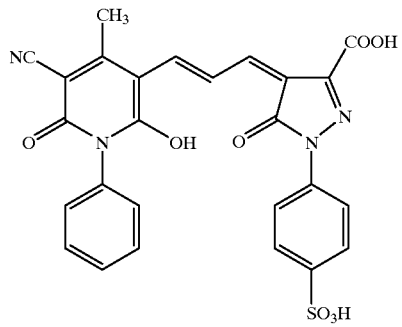

4-(3-(5-Cyano-2-hydroxy-4-methyl-6-oxo-1-phenyl-1,6-dihydropyridin-3-yl)-allyliden)-5-oxo-1-(4-sulfophenyl)-4,5-dihydro-1H-pyrazol-3-carboxylic acid (20)

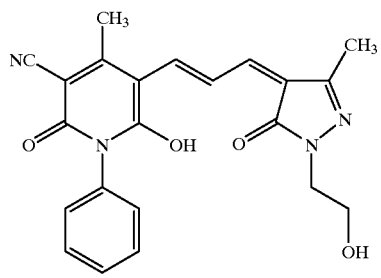

6-Hydroxy-5-(3-(1-(2-hydroxyethyl)-3-methyl-5-oxo-1,5-dihydropyrazol-4-yliden)-propenyl)-4-methyl-2-oxo-1-phenyl-1,2-dihydropyridin-3-carbonitril (21)

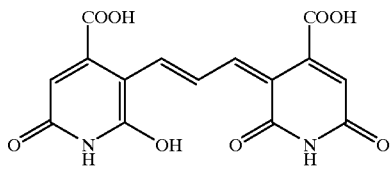

5-(3-(4-Carboxy-2,6-dioxo-1,6-dihydro-2H-pyridin-3-yliden)-propenyl)-6-hydroxy-2-oxo-1,2-dihydropyridin-4-carboxylic acid (22)

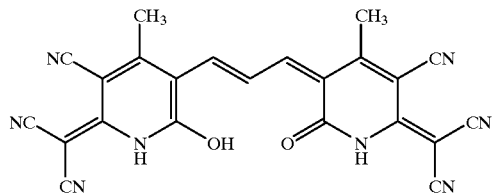

12

2-(3-Cyano-5-(3-(5-cyano-6-dicyanomethylen-4-methyl-2-oxo-1,6-dihydro-2H-pyridin-3-yliden)-propenyl)-6-hydroxy-4-methyl-1H-pyridin-2-yliden)-malononitril (23)

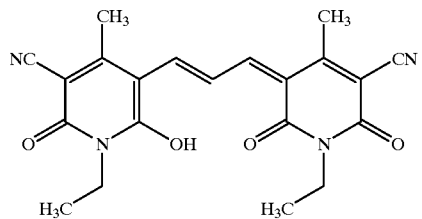

5-(3-(5-Cyano-1-ethyl-4-methyl-2,6-dioxo-1,6-dihydro-2H-pyridin-3-yliden)-propenyl)-1-ethyl-6-hydroxy-4-methyl-2-oxo-1,2-dihydropyridin-3-carbonitril (24)

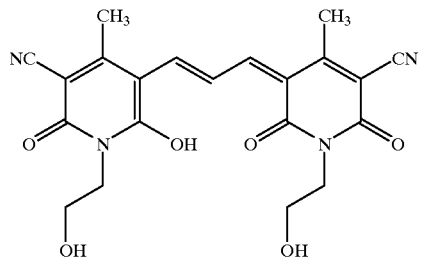

5-(3-(5-Cyano-1-(2-hydroxyethyl)4-methyl-2,6-dioxo-1,6-dihydro-2H-pyridin-3-yliden)-propenyl)-6-hydroxy-1-(2-hydroxyethyl)-4-methyl-2-oxo-1,2-dihydropyridin-3-carbonitril (25)

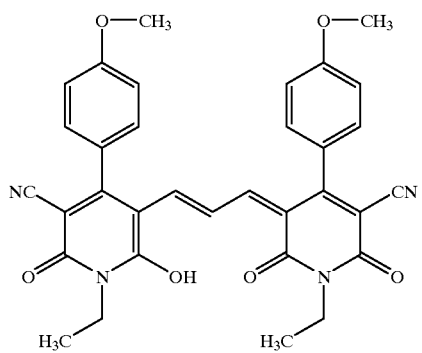

5-(3-(5-Cyano-1-ethyl-4-(4-methoxyphenyl)-2,6-dioxo-1,6-dihydro-2H-pyridin-3-yliden)-propenyl)-1-ethyl-6-hydroxy-4-(4-methoxyphenyl)-2-oxo-1,2-dihydropyridin-3-carbonitril (26)

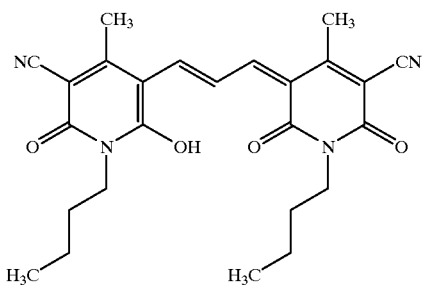

1-Butyl-5-(3-(1-butyl-5-cyano-4-methyl-2,6-dioxo-1,6-dihydro-2H-pyridin-3-yliden)-propenyl)-6-hydroxy-4-methyl-2-oxo-1,2-dihydropyridin-3-carbonitril (27)

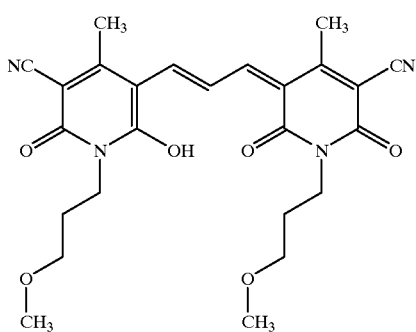

5-(3-(5-Cyano-1-(3-methoxy-propyl)-4-methyl-2,6-dioxo-1,6-dihydro-2H-pyridin-3-yliden)-propenyl)-6-hydroxy-1-(3-methoxy-propyl)-4-methyl-2-oxo-1,2-dihydropyridin-3-carbonitril (28)

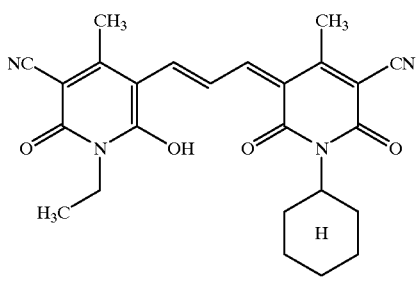

5-(3-(5-Cyano-1-cyclohexyl-4-methyl-2,6-dioxo-1,6-dihydro-2H-pyridin-3-yliden)-propenyl)-1-ethyl-6-hydroxy-4-methyl-2-oxo-1,2-dihydropyridin-3-carbonitril (29)

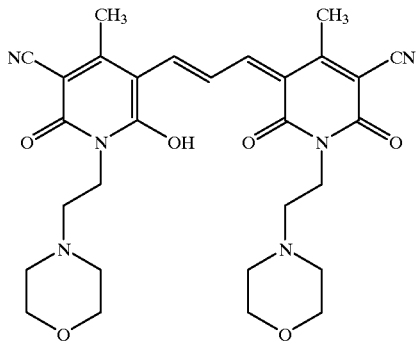

5-(3-(5-Cyano-4-methyl-1-(2-morpholin-4-yl-ethyl)-2,6-dioxo-1,6-dihydro-2H-pyridin-3-yliden)-propenyl)-6-hydroxy-4-methyl-1-(2-morpholin-4-yl-ethyl)-2-oxo-1,2-dihydropyridin-3-carbonitril (30)

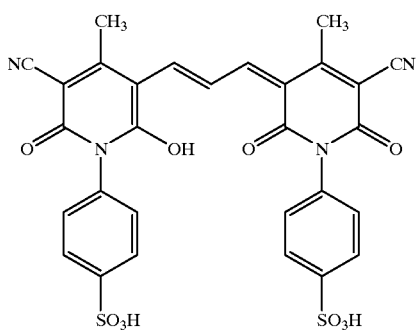

5-(3-(5-Cyano-4-methyl-2,6-dioxo-1-(4-sulfophenyl)-1,6-dihydro-2H-pyridin-3-yliden)-propenyl)-6-hydroxy-4-methyl-2-oxo-1-(4-sulfophenyl)-1,2-dihydropyridin-3-carbonitril (31)

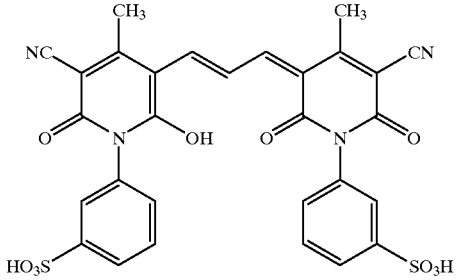

5-(3-(5-Cyano-4-methyl-2,6-dioxo-1-(3-sulfophenyl)-1,6-dihydro-2H-pyridin-3-yliden)-propenyl)-6-hydroxy-4-methyl-2-oxo-1-(3-sulfophenyl)-1,2-dihydropyridin-3-carbonitril (32)

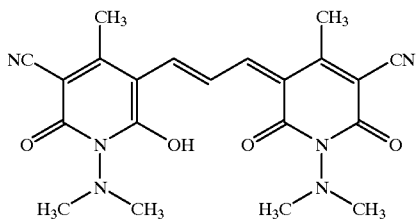

5-(3-(5-Cyano-1-dimethylamino-4-methyl-2,6-dioxo-1,6-dihydro-2H-pyridin-3-yliden)-propenyl)-1-dimethylamino-6-hydroxy-4-methyl-2-oxo-1,2-dihydropyridin-3-carbonitril (33)

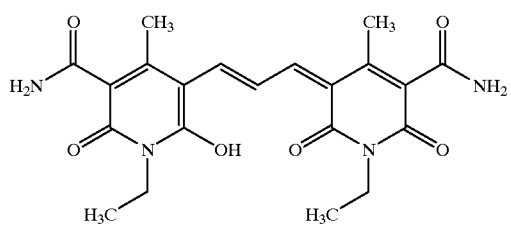

5-(3-(5-Carbamoyl-1-ethyl-4-methyl-2,6-dioxo-1,6-dihydro-2H-pyridin-3-yliden)-propenyl)-1-ethyl-6-hydroxy-4-methyl-2-oxo-1,2-dihydropyridin-3-carboxamide (34)

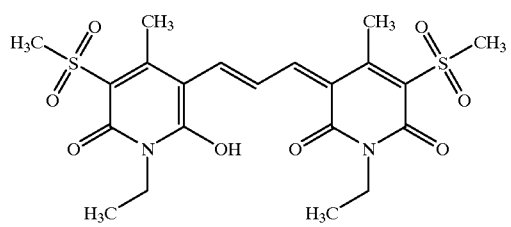

1-Ethyl-3-(3-(1-ethyl-2-hydroxy-5-methansulfonyl-4-methyl-6-oxo-1,6-dihydro-pyridin-3-yl)-allyliden)-5-methansulfonyl-4-methyl-3H-pyridin-2,6-dione (35)

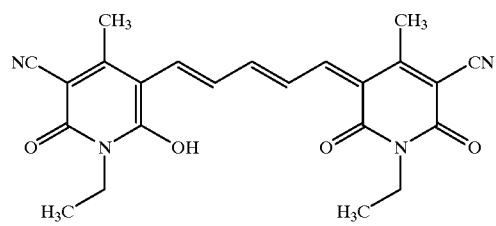

5-(5-(5-Cyano-1-ethyl-4-methyl-2,6-dioxo-1,6-dihydro-2H-pyridin-3-yliden)-penta-1,3-dienyl)-1-ethyl-6-hydroxy-4-methyl-2-oxo-1,2-dihydropyridin-3-carbonitril (36)

Particularly preferred among the aforesaid dyes are compounds of formula (II) to (IV) wherein R1 and R1' are equal and denote a sulfophenyl or hydroxyethyl group;

R2 and R2' are equal and denote hydrogen or a methyl, carboxyl, carboxylate ester or amino group;

R3 and R3' independently of each other denote hydrogen or a straight-chain C1–C4 alkyl group, or a methoxyethyl, hydroxyethyl, sulfoethyl, phenyl or sulfophenyl group;

R4 and R4' are equal and denote hydrogen or a nitrilo or carboxamido group;

R5 and R5' are equal and denote a methyl or carboxyl group;

R6 denotes a phenyl, sulfophenyl, methyl or hydroxyethyl group;

R7 denotes hydrogen or a methyl, carboxyl, carboxylate ester or amino group;

R8 denotes hydrogen or a straight-chain C1–C4 alkyl group or a methoxyethyl, hydroxyethyl, sulfoethyl, phenyl or sulfophenyl group;

R9 denotes a nitrilo group;

R10 denotes a methyl or carboxyl group;

Z denotes oxygen;

R denotes a hydrogen atom or a methyl group, and the indices m and n each equal 0, 1 or 2, the sum of m and n amounting to a maximum of 2.

The dyes with a pronounced anionogenic character (this applies particularly to dyes containing acid functions, such as sulfonic acid or carboxyl groups) can also be used in the form of their physiologically tolerated salts. Particularly suitable are the following compounds:

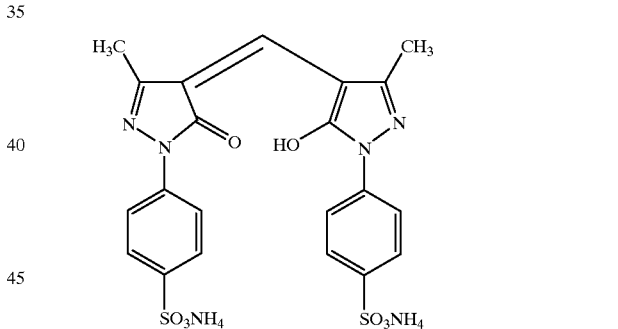

Diammonium-4-(5-hydroxy-3-methyl-1-(4-sulfophenyl)-1H-pyrazol-4-yl-methylen)-5-methyl-2-(4-sulfophenyl)-2,4-dihydro-pyrazol-3-one (3a)

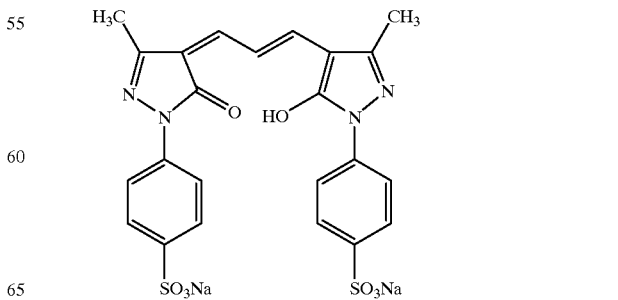

17

Disodium-4-(3-(5-hydroxy-3-methyl-1-(4-sulfophenyl)-1H-pyrazol-4-yl)-allyliden)-5-methyl-2-(4-sulfophenyl)-2,4-dihydropyrazol-3-one (7a)

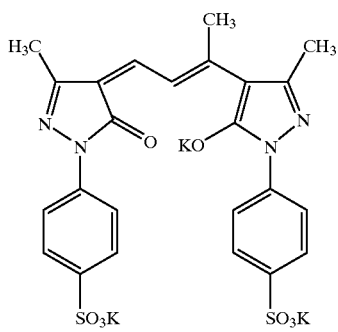

Tripotassium-4-(3-(5-hydroxy-3-methyl-1-(4-sulfophenyl)-1H-pyrazol-4-yl)-but-2-enyliden)-5-methyl-2-(4-sulfophenyl)-2,4-dihydropyrazol-3-one (8a)

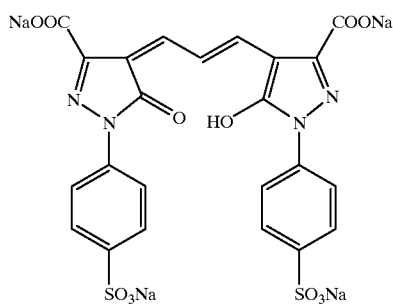

Tetrasodium-4-(3-(3-carboxy-5-oxo-1-(4-sulfophenyl)-1,5-dihydropyrazol-4-yliden)propenyl)-5-hydroxy-1-(4-sulfophenyl)-1H-pyrazol-3-carboxylic acid (9a)

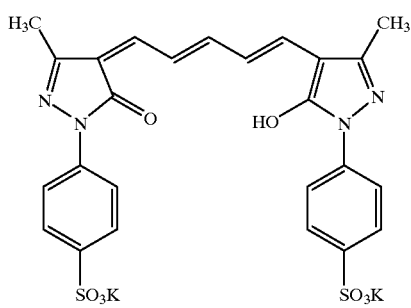

18

Dipotassium-4-(5-(5-hydroxy-3-methyl-1-(4-sulfophenyl)-1H-pyrazol-4-yl)-penta-2,4-dienyliden)-5-methyl-2-(4-sulfophenyl)-2,4-dihydropyrazol-3-one (14a)

Dipotasium-4-(5-(3-carboxy-5-oxo-1-(4-sulfophenyl)-1,5-dihydro-pyrazol4-yliden)penta-1,3-dienyl)-5-hydroxy-1-(4-sulfophenyl)-1H-pyrazol-3-carbopxylic acid (15a)

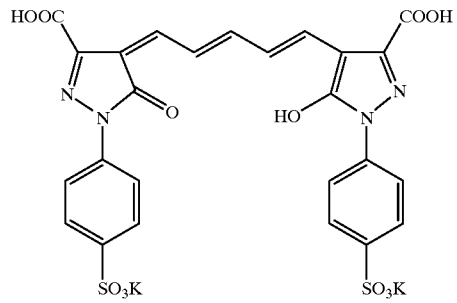

Sodium-5-(3-(5-cyano-1-ethyl-4-methyl-2,6-dioxo-1,6-dihydro-2H-pyridin-3-yliden)propenyl)-1-ethyl-6-hydroxy-4-methyl-2-oxo-1,2-dihydropyridin-3-carbonitrile (24a)

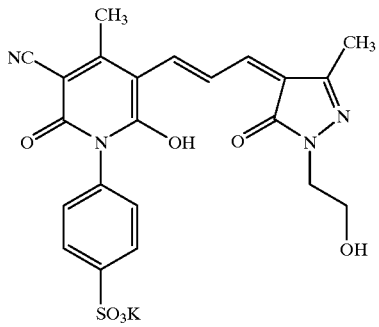

Potasium-6-hydroxy-5-(3-(1-(2-hydroxyethyl)-3-methyl-5-oxo-1,5-dihydropyrazol-4-yliden)propenyl)-4-methyl-2-oxo-1-(4-sulfophenyl)-1,2-dihydropyridin-3-carbonitrile (17a)

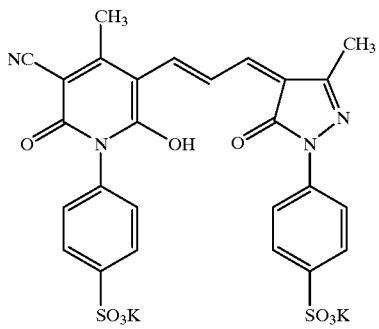

Potasium-6-hydroxy-4-methyl-5-(3-(3-methyl-5-oxo-1-(4-sulfophenyl)-1,5-dihydropyrazol-4-yliden)propenyl)-2-oxo-1-(4-sulfophenyl)-1,2-dihydropyridin-3-carbonitrile (18a)

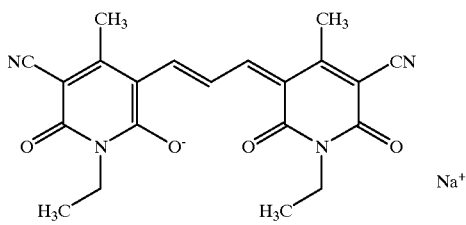

Natrium-5-(3-(5-cyano-1-ethyl-4-methyl-2,6-dioxo-1,6-dihydro-2H-pyridin-3-yliden)-propenyl)-1-ethyl-6-hydroxy-4-methyl-2-oxo-1,2-dihydro-pyridin-3-carbonitrile (24a)

In the colorant for keratin fibers according to the invention, the oxonol dyes of formulas (Ia)/(Ib) to (IV) are contained in a total amount from 0.01 to 5 wt % and preferably from 0.5 to 4 wt %.

Carriers commonly used in cosmetic systems can be added to increase color intensity. Suitable compounds are, for example, benzyl alcohol, vanillin or isovanillin. Other carriers are described in German Unexamined Patent Application DE-OS 196 18 595 the disclosures of which are hereby incorporated by reference.

The hair colorants according to the invention can be used in the form of, for example, a solution, particularly an aqueous-alcoholic solution, or a cream, gel or emulsion. Suitable solvents besides water are, for example, the lower aliphatic monohydric or polyhydric alcohols, their esters and ethers or mixtures of these solvents with each other or with water. The maximum boiling point of the aforesaid solvents is about 400° C., a boiling point of 20° C. to 250° C. being preferred.

It is also possible to dispense said colorants with the aid of a sprayer or some other suitable pumping or spraying device or, in admixture with conventional propellants liquefied under pressure, dispense them in the form of an aerosol spray or aerosol foam from a pressurized container.

The pH of the colorants of the invention is from 2 to 11, a pH of 2.5 to 8 being particularly preferred. An alkaline pH is preferably obtained with ammonia, but an organic amine, for example monoethanolamine or triethanolamine, can be used in place of ammonia. To obtain an acidic pH, on the other hand, an organic or inorganic acid can be used, for example hydrochloric, sulfuric, phosphoric, ascorbic, glycolic or lactic acid.

Naturally, the aforedescribed colorants can optionally contain other common additives suitable for such colorants, for example hair-care agents, wetting agents, thickeners, softeners, preservatives and perfumes as well as other additives listed in the following.

The colorants according to the invention can also contain wetting agents or emulsifiers from the classes of anionic, amphoteric, nonionic or zwitterionic surface-active agents, such as fatty alcohol sulfates, alkanesulfonates, alkylbenzenesulfonates, alkylbetaines, α-olefinsulfonates, ethoxylated fatty alcohols, ethoxylated nonylphenols, fatty alkanolamines, ethoxylated fatty esters, fatty alcohol polyglycol ether sulfates, alkyl polyglucosides, thickeners such as the higher fatty alcohols, starch, alginates, bentonites, cellulose derivatives, vaseline, paraffin oil and fatty acids, water-soluble polymeric thickeners such as various types of natural gums, guar gum, xanthan gum, carob bean flour, pectin, dextran, agar, amylose, amylopectin, dextrins, clays or fully synthetic hydrocolloids, such as polyvinyl alcohol, furthermore hair-care agents such as lanolin derivatives, cholesterol, pantothenic acid, water-soluble polymers, protein derivatives, provitamins, vitamins, plant extracts, sugar and betaine as well as auxiliary agents such as humectants, electrolytes, antioxidants, fatty amides, sequestrants, film-forming agents and preservatives.

The aforedescribed colorants can also contain natural or synthetic polymers or modified natural polymers whereby the keratin fiber is strengthened while it is being colored. Such agents are generally referred to as shade or color enhancers. Suitable among the synthetic polymers known to be used in cosmetics for this purpose are, for example, polyvinylpyrrolidone, polyvinyl acetate, polyvinyl alcohol, or polyacrylic compounds, such as polyacrylic acid or polymethacrylic acid, polyacrylonitrile, polyvinyl acetates and copolymers of such compounds, for example polyvinylpyrrolidone-vinyl acetate copolymers. Suitable natural or modified natural polymers are, for example, chitosan (deacetylated chitin) or chitosan derivatives.

The said constituents are used in amounts that are normal for such purposes. For example, the wetting agents and emulsifiers are used at a concentration of about 0.5 to 30 wt %, the thickeners in an amount from about 0.1 to 25 wt % and the hair-care agents from about 0.1 to 5 wt %.

The aforesaid polymers can be used in the colorants of the invention in amounts that are normal for such colorants, particularly in an amount from about 1 to 5 wt %.

For hair coloring, the colorants of the invention are applied to the hair in the usual manner in an amount sufficient for hair coloring, in general in an amount from about 50 to 150 grams. After an exposure time sufficient for hair coloring, usually about 10 to 45 min at 20 to 25° C. and preferably 15 to 30 min at about 40° C., the hair is rinsed with water, optionally washed with a shampoo and/or an aqueous solution of a weak organic acid, for example citric or tartaric acid, again rinsed and then dried.

The colorant with the additional strengthening action is used in a known and conventional manner by wetting the hair with it, styling the hair and then drying.

As regards the scope of possible coloring, the hair colorants according to the invention offer, depending on the type and composition of the oxonol dye used, a broad spectrum of different color shades ranging from natural shades to highly fashionable, bright shades. The advantageous properties of the novel dyes manifest themselves particularly on light-damaged and weather-damaged or permanently waved hair.

Because the colorants according to the invention contain exclusively oxonol dyes which are structurally related and, hence, mutually compatible, uniform coloring and decoloration results are achieved.

The coloring system according to the invention is furthermore characterized in that the hair coloring can be reversed at any time. In this respect, it is particularly advantageous that the decoloration restores the original pigmentation of the treated hair, it being irrelevant in practice whether the original pigmentation is the natural hair color or was achieved by oxidative hair coloring. It is thus possible to change the natural hair color to a permanent hair color for a self-selected time period and then, at the end of this period, to restore the natural color in practically unchanged form.

The object of the present application is therefore also a method for temporary coloring of hair ("ON/OFF shading") whereby uncolored or oxidatively colored hair is colored with the colorant according to the invention in the afore-described manner and later (at any time desired by the user) is decolorized with a reducing agent or oxidant.

The dyes of formulas (Ia)/(Ib) to (IV) can be completely decolorized reductively by the action of, for example, suitable reducing agents, for example sulfites, metabisulfites, or hydrogen sulfites, for example alkali metal sulfites, alkali metal hydrogen sulfites or alkali metal metabisulfites (for example, sodium sulfite, sodium metabisulfite, potassium metabisulfite), ammonium sulfite or ammonium hydrogen sulfite, or with suitable oxidants such as, for example, commercial persulfate-containing hair-bleaching powders. The hair-bleaching powders as a rule contain from 5 to 50 wt % and preferably from 15 to 30 wt % of ammonium persulfate or alkali metal persulfate or a mixture of ammonium and alkali metal persulfates. The decolorization is preferably carried out reductively by use of the aforesaid decolorizing agents (particularly with ammonium sulfite or ammonium hydrogen sulfite), the use the aforesaid reducing agents in combination with other reducing agents, for example with reductones and/or thiols being particularly preferred.

Depending on the color to be decolorized and the temperature (about 20 to 50° C.), the time required for the decolorizing agent to act is from 5 to 45 minutes and particularly from 5 to 30 minutes. The decolorizing process can be accelerated by heating. At the end of the time of exposure to the decolorizing agent, the hair is rinsed with water, optionally washed with a shampoo and/or treated with a rinse, preferably a neutral or weakly acidic rinse, and then dried. Both the shampoo and the rinse can contain a reductone, for example ascorbic acid.

After decolorization, the original color shade is thus restored. If, on the other hand, a hair-bleaching agent consisting of a hydrogen peroxide solution, preferably a 6–12% hydrogen peroxide solution is used, the oxonol dyes are completely decolorized and, in addition, the hair is brightened (bleached).

In a preferred embodiment of the invention, the hair colorants of the invention and the decolorizing agent are packaged in the form of a 2-component kit, it being particularly advantageous if the decolorizing agent is specifically intended for the hair colorant of the invention used to color the hair.

The monomethine oxonol dyes (m=n=0) can be prepared from the corresponding heterocyclic compounds and trialkyl orthoesters or formamides as bridge precursors. Numerous compounds have been described by B. Schied, J. prakt. Chem. 157, p. 203 ff (1941) and by S. Hünig, Annalen 574, p. 106 ff (1951) and in references cited therein. To prepare the trimethine oxonols (m+n=1) according to DE-OS 20 12 050, trimethoxypropane, trimethoxypropene or malonaldehyde dianil can be used. Pentamethine oxonols (m+n=2) can be prepared from N-acceptor-substituted pyridinium salts by opening the pyridine ring (Zincke cleavage) or a related derivative, for example glutaconaldehyde dianil. A complete summary of such preparations can be found in Houben-Weyl 7/1, 4th edition (1954), on pages 263 ff and in the literature cited therein.

EXAMPLES

Example 1

Method for Preparing Diammonium-4-(5-hydroxy-3-methyl-1-(4-sulfophenyl)-1H-pyrazol-4-ylmethylene)-5-methyl-2-(4-sulfophenyl)-2,4-dihydropyrazol-3-one (3a)

50.85 g of 3-methyl-1-(4-sulfophenyl)-2-pyrazolin-5-one and 30.8 g of ammonium acetate were suspended in 400 mL of acetic acid and heated to 90° C. Then, 10.6 g of trimethyl orthoformate was added dropwise with agitation upon which the reaction mixture spontaneously assumed a yellow color. The mixture was allowed to agitate for an additional 4 hours after which it was cooled to room temperature. The precipitated dye was collected by suction filtration, washed with isopropanol and dried. This yielded 50.8 g of diammonium-4-(5-hydroxy-3-methyl-1-(4-sulfophenyl)-1H-pyrazol-4-ylmethylene)-5-methyl-2-(4-sulfophenyl)-2,4-dihydropyrazol-3-one (3a) as a bright yellow product.

| | |
|---|---|
| Melting point: | >250° C. |
| $\lambda_{max}$ (H$_2$O): | 432 nm |
| $\epsilon$ | 36500 |
| $^1$H-NMR (D$_2$O): | $\sigma$ = 7.70 (d, $^3J_{HH}$ = 8.6 Hz, 4H); 7.59 (d, $^3J_{HH}$ = 8.6 Hz, 4H); 6.89 (s, 1H); 4,68 (HOD exchange signal); 1.89 ppm (s, 6H). |

Example 2

Colorant

| |
|---|
| 5.0 g of ethanol |
| 1.5 g of glycolic acid |
| 2.0 g of sodium cocoamphoacetate (50% aqueous solution) |
| 5.0 g of benzyl alcohol |
| 1.7 g of diammonium-4-(5-hydroxy-3-methyl-1-(4-sulfophenyl)-1H-pyrazol-4-ylmethylene)-5-methyl-2-(4-sulfophenyl)-2,4-dihydropyrazol-3-one (3a) |
| to 100.0 g water, demineralized |

The foregoing coloring solution was applied to bleached hair. After an exposure time of 20 minutes at 40° C., the hair was washed with water and dried. The hair had a bright yellow color.

Example 3

Colorant

| |
|---|
| 5.0 g of ethanol |
| 1.5 g of glycolic acid |
| 2.0 g of sodium cocoamphoacetate (50% aqueous solution) |
| 5.0 g of benzyl alcohol |
| 1.4 g of tripotassium 4-(3-(5-hydroxy-3-methyl-1-(4-sulfophenyl)-1H-pyrazol-4-yl)-2-butenylidene)-5-methyl-2-(4-sulfophenyl)-2,4-dihydropyrazol-3-one (8a) |
| to 100.0 g water, demineralized. |

The colorant solution was applied to bleached hair. After an exposure time of 20 min at 40° C., the hair was washed with water and dried. The hair had a bright red color.

Example 4

Colorant

| |
|---|
| 5.0 g of ethanol |
| 1.5 g of glycolic acid |
| 2.0 g of sodium cocoamphoacetate (50% aqueous solution) |
| 5.0 g of benzyl alcohol |
| 1.2 g of sodium 5-(3-(5-cyano-2-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile (24a) |
| to 100.0 g water, demineralized |

The colorant solution was applied to bleached hair. After an exposure time of 20 min at 40° C., the hair was washed with water and dried. The hair had an intense blue color.

Example 5

Colorant

---
5.0 g of ethanol
1.5 g of glycolic acid
2.0 g of sodium cocoamphoacetate (50% aqueous solution)
5.0 g of benzyl alcohol
1.8 g of dipotassium 4-(5-(3-carboxy-5-oxo-1-(4-sulfophenyl(-1,5-dihydropyrazol-4-ylidene)-penta-1,3-dienyl)-5-hydroxy-1-(4-sulfophenyl)-1H-pyrazol-3-carboxylate (15a)
to 100.0 g water, demineralized
---

The colorant solution was applied to bleached hair. After an exposure time of 20 min at 40° C., the hair was washed with water and dried. The hair had a blue-green color.

Example 6

Colorant

---
5.0 g of ethanol
1.5 g of glycolic acid
2.0 g of sodium cocoamphoacetate (50% aqueous solution)
5.0 g of benzyl alcohol
0.7 g of diammonium-4-(5-hydroxy-3-methyl-1-(4-sulfophenyl)-1H-pyrazol-4-ylmethylene)-5-methyl-2-(4-sulfophenyl)-2,4-dihydropyrazol-3-one (3a)
0.2 g of tetrasodium 4-(3-(3-carboxy-5-hydroxy-1-(4-sulfophenyl-1H-pyrazol-4-yl)-2-propylidene)-5-carboxy-2-(4-sulfophenyl)-2,4-dihydropyrazol-3-one (9a)
to 100.0 g water, demineralized.
---

The colorant solution was applied to bleached hair. After an exposure time of 20 min at 40° C., the hair was washed with water and dried. The hair color was of a medium chestnut shade.

Example 7

Reductive Decolorization of Fibers Colored with Oxonol Dyes a) For decolorization, the hair dyed as described in Examples 2 to 6 was treated with a 10% aqueous ammonium bisulfite solution. Decolorization occurred within a few minutes. The hair was thoroughly rinsed with water and then dried. The original color of the hair was restored in all cases (97 to 99% decolorization).

b) In addition, the decolorizability of other fibers (silk, nylon 66) was compared with that of hair. To this end, the fibers were colored with a colorant as described in Examples 2 to 6 and then decolorized by the method described under a). Because of the poor decolorizability of the other fibers, a decolorization time of 30 minutes was used. The results are summarized in the following table.

In contrast to hair which can be completely decolorized, silk (which is also a keratin fiber) and nylon 66 (a synthetic fiber) can be decolorized only partly, if at all.

|  | L* | a* | b* | ΔE½ | Decolorization, % |
|---|---|---|---|---|---|
| Fibers colored as per Ex. 2 |  |  |  |  |  |
| Hair | 86,23 | −0,91 | 11,77 |  |  |
| colored | 81,77 | −4,87 | 79,05 | 67,54 |  |

-continued

|  | L* | a* | b* | ΔE½ | Decolorization, % |
|---|---|---|---|---|---|
| decolorized | 84,32 | −2,17 | 13,72 | 65,44 | 97 |
| Silk | 85,69 | 1,33 | 9,50 |  |  |
| colored | 80,16 | 0,34 | 82,83 | 73,94 |  |
| decolorized | 84,30 | −4,74 | 45,26 | 38,14 | 52 |
| Nylon 66 | 91,71 | −0,67 | 5,50 |  |  |
| colored | 83,09 | 0,62 | 81,82 | 76,82 |  |
| decolorized | 88,72 | −10,47 | 64,32 | 21,47 | 28 |
| Fibers colored as per Ex. 3 |  |  |  |  |  |
| Hair | 86,23 | −0,91 | 11,77 |  |  |
| colored | 19,76 | 14,86 | −25,62 | 77,88 |  |
| decolorized | 84,71 | −1,42 | 10,94 | 76,29 | 98 |
| Silk | 85,69 | 1,33 | 9,50 |  |  |
| colored | 31,42 | 47,39 | 8,03 | 71,53 |  |
| decolorized | 45,41 | 61,49 | −8,26 | 25,69 | 36 |
| Nylon 66 | 91,71 | −0,67 | 5,50 |  |  |
| colored | 38,21 | 51,20 | −5,39 | 75,31 |  |
| decolorized | 54,89 | 66,00 | −12,50 | 23,41 | 31 |
| Fibers colored as per Ex. 4 |  |  |  |  |  |
| Hair | 86,23 | −0,91 | 11,77 |  |  |
| colored | 19,76 | 14,86 | −25,62 | 77,88 |  |
| decolorized | 84,71 | −1,42 | 8,94 | 75,35 | 97 |
| Nylon 66 | 91,71 | −0,67 | 5,50 |  |  |
| colored | 22,25 | 22,83 | −34,77 | 83,66 |  |
| decolorized | 32,12 | 38,37 | −62,73 | 33,48 | 40 |
| Silk | 85,69 | 1,33 | 9,50 |  |  |
| colored | 24,05 | 15,20 | −20,23 | 69,93 |  |
| decolorized | 65,83 | −0,13 | −21,30 | 44,52 | 64 |
| Fibers colored as per Ex. 5 |  |  |  |  |  |
| Hair | 86,23 | −0,91 | 11,77 |  |  |
| colored | 27,83 | −3,84 | −17,81 | 65,53 |  |
| decolorized | 85,60 | −2,09 | 11,09 | 64,62 | 99 |
| Silk | 85,69 | 1,33 | 9,50 |  |  |
| colored | 24,85 | 0,41 | −9,92 | 63,98 |  |
| decolorized | 77,26 | −8,80 | 9,66 | 56,70 | olive-green[1] |
| Nylon 66 | 91,71 | −0,67 | 5,50 |  |  |
| colored | 34,52 | −6,35 | −15,50 | 61,19 |  |
| decolorized | 56,33 | −20,57 | −13,61 | 26,10 | 43 |
| Fibers colored as per Ex. 6 |  |  |  |  |  |
| Hair | 86,23 | −0,91 | 11,77 |  |  |
| colored | 31,46 | 20,46 | −2,99 | 60,62 |  |
| decolorized | 81,51 | −4,14 | 15,79 | 58,85 | 97 |
| Silk | 85,69 | 1,33 | 9,50 |  |  |
| colored | 36,22 | 45,46 | 7,48 | 66,66 |  |
| decolorized | 84,42 | −2,86 | 34,77 | 73,50 | yellow[1] |
| Nylon 66 | 91,71 | −0,67 | 5,50 |  |  |
| colored | 49,84 | 41,20 | 11,37 | 59,50 |  |
| decolorized | 69,63 | 37,24 | 31,72 | 28,66 | orange[1] |

[1] No fiber decolorization, but color change

Example 8

Oxidative Decolorization of Hair Colored with Oxonol Dyes

For decolorization, medium-blond hair colored with a colorant as described in Example 4 was treated with a commercial 25% aqueous bleaching agent (1:1 combination of ammonium persulfate/alkali metal persulfate) without added hydrogen peroxide. After an exposure time of a few minutes, the hair was thoroughly rinsed and dried. The hair had once again its original color.

|   | L* | a* | b* | ΔE½ | Decoloriza-tion, % |
|---|---|---|---|---|---|
| Hair | 36.75 | 7.25 | 12.71 | | |
| colored | 18.68 | 3.88 | −6.81 | 26.15 | |
| decolorized | 36.00 | 8.10 | 13.33 | 26.90 | 100 |

Example 9
Oxidative Decolorization and Simultaneous Bleaching of Hair Colored with Oxonol Dyes For decolorization and simultaneous bleaching, medium-blond hair colored with a colorant as described in Example 4 was treated with a 1:1 mixture of a commercial 50% aqueous hair-bleaching agent (1:1 combination of ammonium persulfate/alkali metal persulfate) and a 6% aqueous hydrogen peroxide solution. After an exposure time of 10 min, the hair was thoroughly rinsed and dried. In this manner, the hair was simultaneously decolorized and additionally bleached.

|   | L* | a* | b* | ΔE½ | Decoloriza-tion, %*) |
|---|---|---|---|---|---|
| Hair | 36.75 | 7.25 | 12.71 | | |
| colored | 18.68 | 3.88 | −6.81 | 26.15 | |
| decolorized | 56.73 | 9.37 | 29.22 | 52.69 | 202 |

*)Note: The calculated degree of decolorization of 202% is made up of the sum of the decolorization of the oxonol dye and the additional brightening of the natural pigmentation (bleaching).

Example 10
Colorant

---
5.0 g of ethanol
1.5 g of glycolic acid
2.0 g of sodium cocoamphoacetate (50% aqueous solution)
5.0 g of benzyl alcohol
1.4 g of disodium 4-(3-(5-hydroxy-3-methyl-1-(4-sulfophenyl)-1H-pyrazol-4-yl)allylidene)-5-methyl-2-(4-sulfophenyl-2,4-dihydropyrazol-3-one (7a)
0.2 g of dipotassium 6-hydroxy-4-methyl-5-(3-(3-methyl-5-oxo-1-(sulfophenyl)-1,5-dihydropyrazol-4-ylidene)propenyl)-2-oxo-1-(4-sulfophenyl)-1,2-dihydropyridin-3-carbonitrile (18a)
to 100.0 g water, demineralized.

---

The colorant solution was applied to bleached hair. After an exposure time of 20 min at 40° C., the hair was washed with water and dried. The hair had a brighter copper shade.

For decolorization, the hair was treated with a 10% aqueous sodium sulfite solution. Decolorization occurred after a few minutes. The hair was then thoroughly washed and dried. The hair retained a light-beige highlight.

|   | L* | a* | b* | ΔE½ | Decoloriza-tion, % |
|---|---|---|---|---|---|
| Hair | 86.23 | −0.91 | 11.77 | | |
| colored | 40.19 | 39.35 | 21.55 | 61.94 | |
| decolorized | 79.06 | 8.29 | 1.42 | 53.67 | 87 |

Example 11
Colorant

---
5.0 g of ethanol
1.5 g of glycolic acid
2.0 g of sodium cocoamphoacetate (50% aqueous solution)
5.0 g of benzyl alcohol
1.4 g of diammonium-4-(5-hydroxy-3-methyl-1-(4-sulfophenyl)-1H-pyrazol-4-ylmethylene)-5-methyl-2-(4-sulfophenyl)-2,4-dihydropyrazol-3-one (3a)
0.5 g of dipotassium 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazol-3-carboxylate (15a)
to 100.0 g water, demineralized

---

The colorant solution was applied to bleached hair. After an exposure time of 20 min at 40° C., the hair was washed with water and dried. The resulting hair had a green color.

For decolorization, the hair was treated with a 10% aqueous sodium bisulfite solution. Decolorization occurred after a few minutes. The hair was then thoroughly washed and dried. The hair retained a light-beige highlight.

|   | L* | a* | b* | ΔE½ | Decoloriza-tion, % |
|---|---|---|---|---|---|
| Hair | 86.23 | −0.91 | 11.77 | | |
| colored | 44.10 | −30.15 | 14.76 | 51.37 | |
| decolorized | 83.05 | −9.21 | 17.59 | 44.31 | 86 |

Example 12
Colorant

---
5.0 g of ethanol
1.5 g of glycolic acid
2.0 g of sodium cocoamphoacetate (50% aqueous solution)
5.0 g of benzyl alcohol
1.4 g of diammonium-4-(5-hydroxy-3-methyl-1-(4-sulfophenyl)-1H-pyrazol-4-ylmethylene)-5-methyl-2-(4-sulfophenyl)-2,4-dihydropyrazol-3-one (3a)
0.2 g of tetrasodium 4-(3-(3-carboxy-5-hydroxy-1-(4-sulfophenyl)-1H-pyrazol-4-yl)2-propylidene)-5-carboxy-2-(4-sulfophenyl)-2,4-dihydropyrazol-3-one (9a)
to 100.0 g water, demineralized.

---

The colorant solution was applied to bleached hair. After an exposure time of 20 min at 40° C., the hair was washed with water and dried. The hair color was of a medium chestnut shade.

For decolorization, the hair was treated with an aqueous solution containing 5% of sodium sulfite and 5% of ascorbic acid. Decolorization occurred after a few minutes. The hair was then thoroughly washed and dried. The hair retained a pale-yellow highlight.

|   | L* | a* | b* | ΔE½ | Decoloriza-tion, % |
|---|---|---|---|---|---|
| Hair | 86.23 | −0.91 | 11.77 | | |
| colored | 55.46 | 40.80 | 37.16 | 57.72 | |
| decolorized | 85.18 | −2.42 | 18.08 | 55.81 | 97 |

Example 13
Colorant

---
5.0 g of ethanol
1.5 g of glycolic acid
2.0 g of sodium cocoamphoacetate (50% aqueous solution)
5.0 g of benzyl alcohol
0.8 g of diammonium-4-(5-hydroxy-3-methyl-1-(4-sulfophenyl)-1H-pyrazol-4-ylmethylene)-5-methyl-2-(4-sulfophenyl)-2,4-dihydropyrazol-3-one (3a)
0.2 g of dipotassium 6-hydroxy-4-methyl-5-(3-(3-methyl-5-oxo-1-(sulfophenyl)-1,5-dihydropyrazol-4-ylidene)propenyl)-2-oxo-1-(4-sulfophenyl)-1,2-dihydropyridine-3-carbonitrile (18a)
0.7 g of tetrasodium 4-(3-(3-carboxy-5-hydroxy-1-(4-sulfophenyl)-1H-pyrazol-4-yl)2-propylidene)-5-carboxy-2-(4-sulfophenyl)-2,4-dihydropyrazol-3-one (9a)
0.4 g of dipotassium-4-(3-(5-hydroxy-3-methyl-1-(4-sulfophenyl)-1H-pyrazol-4-yl)penta-2-enylidene)-5-methyl-2-(4-sulfophenyl)-2,4-dihydropyrazol-3-one (14a)
to 100.0 g water, demineralized

---

The colorant solution was applied to bleached hair. After an exposure time of 20 min at 40° C., the hair was washed with water and dried. The hair had the color of anthracite.

For decolorization, the hair was treated with a 10% aqueous ammonium bisulfite solution. Decolorization occurred after a few minutes. The hair was then thoroughly washed and dried. The hair retained a pale-yellow highlight.

|  | L* | a* | b* | ΔE½ | Decolorization, % |
|---|---|---|---|---|---|
| Hair | 86.23 | −0.91 | 11.77 |  |  |
| colored | 25.36 | 10.75 | −5.11 | 64.23 |  |
| decolorized | 81.66 | 3.18 | 9.11 | 58.56 | 91 |

Example 14
Color Change on Oxidatively Colored Hair

Bleached hair that had been colored medium-blond with a commercial oxidative hair colorant was treated with a colorant according to Example 4. After an exposure time of 20 min at 40° C., the hair was washed with water and dried. The hair had an intense eggplant shade.

For decolorization, the hair was treated with a 10% aqueous ammonium bisulfite solution. After a few minutes, the shade of the precolored hair was restored, with additional brightening.

|  | L* | a* | b* | ΔE½ | Decolorization, % |
|---|---|---|---|---|---|
| Oxidatively colored hair | 37.24 | 4.76 | 12.78 |  |  |
| additionally colored | 21.84 | −1.41 | −0.45 | 21.22 |  |
| decolorized | 45.00 | 5.01 | 20.33 | 31.77 | 150*) |

*)Note: The calculated degree of decolorization of 150% is made up of the sum of the decolorization of the oxonol dye and the additional brightening of the previously applied oxidative hair dye.

Example 15
Color Change on Oxidatively Colored Hair

Bleached hair that had been colored medium-blond with a commercial oxidative colorant was treated with the following colorant.

---
5.0 g of ethanol
1.5 g of glycolic acid
2.0 g of sodium cocoamphoacetate (50% aqueous solution)
5.0 g of benzyl alcohol
1.4 g of disodium 4-(3-(5-hydroxy-3-methyl-1-(sulfophenyl)-1H-pyrazol-4-yl)allylidene)-5-methyl-2-(4-sulfophenyl-2,4-dihydropyrazol-3-one (7a)
to 100.0 g water, demineralized

---

After a 20-min exposure at 40° C., the hair was washed and dried. The hair had a brick-red shade.

For decolorization, the hair was treated with a 10% aqueous ammonium bisulfite solution. After a few minutes, the shade of the precolored hair was restored, with additional brightening.

|  | L* | a* | b* | ΔE½ | Decolorization, % |
|---|---|---|---|---|---|
| Oxidatively colored hair | 37.24 | 4.76 | 12.78 |  |  |
| additionally colored | 26.58 | 29.16 | 9.96 | 26.78 |  |
| decolorized | 47.53 | 4.51 | 22.00 | 34.52 | 129*) |

*)Note: The calculated degree of decolorization of 129% is made up of the sum of the decolorization of the oxonol dye and the additional brightening (bleaching) of the oxidative hair dye.

Example 16
Colorant with Carrier

---
5.0 g of ethanol
2.0 g of lactic acid
2.0 g of sodium cocoamphoacetate (50% aqueous solution)
5.0 g of carrier as per the following table
1.2 g of sodium 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile (24a)
to 100.0 g water, demineralized

---

The colorant solution was applied to bleached hair. After an exposure time of 20 min at 40° C., the hair was washed with water and dried. The colorant without the carrier gave a medium-blue shade, whereas the colorants with carrier gave intense blue shades.

| Example | Carrier | L* | a* | b* |
|---|---|---|---|---|
| a | None | 35.18 | 26.57 | −46.26 |
| b | Vanillin | 19.20 | 19.13 | −28.43 |
| c | 2-Hydroxymethylthiophene | 18.22 | 18.77 | −26.96 |
| d | Benzyl alcohol | 18.88 | 13.13 | −22.19 |

The L-value indicates the brightness (in other words, the lower the L value, the higher is the color intensity). The a-value is a measure of the red content (namely, the higher the a-value the higher is the red content). The b-value is a measure of the blue content of the color, the blue content being the higher the more negative is the b-value.

The value of ΔE indicates the difference in color between the untreated and the colored hair or between the colored and the decolorized hair. It is determined as follows:

$$\Delta E_1 = \sqrt{(L_1 - L_0)^2 + (a_1 - a_0)^2 + (b_1 - b_o)^2}$$

$$\Delta E_2 = \sqrt{(L_2 - L_1)^2 + (a_2 - a_1)^2 + (b_2 - b_1)^2}$$

where $L_0$, $a_0$ and $b_0$ are the values measured before coloring or before decolorizing, $L_1$, $a_1$ and $b_1$ are the values after coloring and $L_2$, $a_2$ and $b_2$ the values after decolorization.

The percentage decolorization was determined according to the following expression:

Decolorization, %=($\Delta E_2/\Delta E_1$)×100

Here, $\Delta E_1$ refers to the coloring step and $\Delta E_2$ to the decolorizing step.

Unless otherwise indicated, all percentages given in the present application are by weight.

What is claimed is:

1. A method for coloring hair, said method comprising the steps of:

a) applying to the hair, in an amount sufficient for the coloring of the hair, a colorant, said colorant comprising at least one monomethine or polymethine dye of tautomeric formula (Ia/Ib), or a physiologically tolerated salt thereof, W=L-V'(Ia)⇌W'-L=V(Ib), wherein W=L-V' and W'=L-V are tautomers, and said W and said V each, independently of each other, is a substituted five-member or six-member heterocyclic ring, so that said W and W' are the same and said V and V' are the same, except that said W and said V each have a —C(=O)— group and said W' and said V' each have a =C(OH)— group in place of said —C(=O)— group in said substituted five-member or six-member heterocyclic ring, and wherein said substituted five-member or six-member heterocyclic ring for said W and for said V is each, independently of each other, selected from the group consisting of substituted pyrazolones, substituted pyridones, substituted dioxothiazolines, substituted rhodanines, substituted dioxoimidazolidines and substituted barbituric acid; wherein L represents a bridging group of formula —[—CH=CH—]$_m$—CR=[=CH—CH=]$_n$=, wherein R is hydrogen, a phenyl group, a halogen atom, a methyl group or a carboxamido group, and wherein m and n, independently of each other, are each 0, 1 or 2, with the proviso that n+m does not exceed 2;

b) after the applying of step a), allowing the colorant to act on the hair for a time interval of from 10 to 45 min at 20 to 50° C.; and c) rinsing the hair with water and subsequently drying the hair.

2. The method as defined in claim 1, further comprising, after the applying and the allowing, washing the hair with at least one of a shampoo and an aqueous solution of a weak organic acid and subsequently drying the hair.

3. The method as defined in claim 1, wherein said polymethine dye is a trimethine or a pentamethine dye.

4. The method as defined in claim 1, wherein said at least one monomethine or polymethine dye is selected from the group consisting of dye compounds of the formulas (II) to (IV):

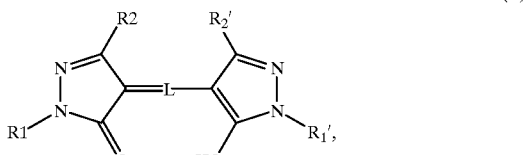

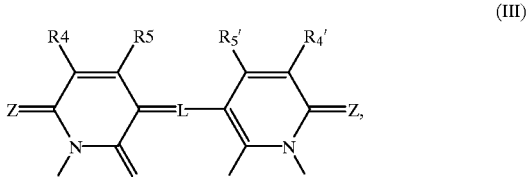

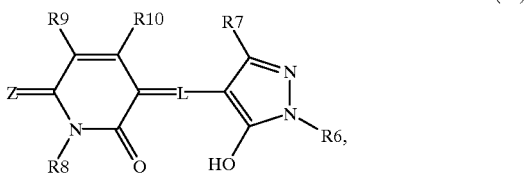

wherein R1, R1' and R6 denote hydrogen; a straight-chain or branched $C_1$- to $C_8$-alkyl group; a hydroxyethyl group; a dihydroxypropyl group; a methoxyethyl group; a carboxyethyl group; a $C_1$- to $C_4$-sulfoalkyl group; a phenyl group; a substituted phenyl group substituted with one or more halogen atoms, with one or two sulfonic acid groups, with one or two carboxyl groups, with one or more straight-chain or branched $C_1$- to $C_8$-alkyl groups or with one or more $C_1$- to $C_8$-alkoxy groups; a benzyl group; a substitute benzyl group substituted with one or more halogen atoms, a $C_1$- to $C_4$-alkyl group, a hydroxy group, a methoxy group, a carboxyl group, a nitro group or an amino group or a five-member or six-member saturated or unsaturated heterocyclic ring; wherein R1 and R1' are equal or different from each other; and wherein R2, R2' and R7 denote hydrogen; a branched or straight chain $C_1$- to $C_6$-alkyl group; a phenyl group; an acylated phenyl group; a sulfonylated phenyl group; an amino group; an acylated amino group; a sulfonylated amino group; an acetyl group; a methoxy group; a carboxyl group; a carboxyl group esterified with a straight-chain or branched $C_1$- to $C_8$-alcohol, with ethylene glycol monomethyl ether or with ethylene glycol monoethyl ether; a carboxamido group; a carboxanilido group; a 2-amino-2-oxyethyl group or a nitrilo group, R2 and R2' being equal or different, and wherein R3, R3' and R8 denote hydrogen; a straight-chain or branched $C_1$- to $C_{11}$-alkyl group; a straight-chain or branched $C_1$- to $C_{11}$-monohydroxyalkyl group; a straight-chain or branched $C_1$- to $C_{11}$-dihydroxyalkyl group; a straight-chain or branched $C_1$- to $C_{11}$-alkoxyalkyl group; a straight-chain or branched $C_1$- to $C_{11}$-monoalkylamino group; an amino group of formula $(CH_2)_x$—NR11R12 wherein x is an integer from 0 to 3 and R11 and R12, independently of each other, denote an $C_1$- to $C_3$-alkyl group, a $C_2$- to $C_4$-sulfoalkyl group, a $C_2$- to $C_8$-carboxyalkyl group; a phenyl group; a substituted phenyl group having one or more halogen atoms, one or two sulfonic acid groups, one or more carboxyl groups, one or more straight-chain or branched $C_1$- to $C_8$-alkyl groups or one or more straight-chain or branched $C_1$- to $C_8$-alkoxy groups; a benzyl group; a substituted benzyl group having one or more halogen atoms, one or more $C_1$- to $C_8$-alkyl groups, a hydroxy group, a methoxy group, a nitro group, or an amino group; a phenylethyl group; a five-member or six-member aromatic or nonaromatic heterocyclic group; a five-member or six-member aromatic or nonaromatic heterocyclic group attached by a methylene group; a pyrrolidino($C_1$- or $C_3$-)alkyl group; a morpholino($C_1$- or $C_3$-)alkyl group; a piperazino($C_1$- or $C_3$-)alkyl group; a piperidino($C_1$- or $C_3$-)alkyl group; a pyridino-($C_1$- or $C_3$-)alkyl group or a trialkylammoniumalkyl group of formula R13-N(R14)$_3^+$ with R13 denoting a $C_1$- to $C_6$-alkylene group, R14 denoting a methyl or ethyl group and with a total number of carbon atoms being equal to 5 to 9, wherein R3 and R3' are equal or different from each other; and wherein R4, R4' and R9 denote hydrogen, a nitro group, a carboxylate ester group, a carboxamido group, a sulfonic acid group, a sulfomethyl group, a methanesulfonyl group, a pyridinium group or an imidazolium group, R4 and R4' being equal or different from each other; and wherein R5, R5' and R10 denote hydrogen, a $C_1$- to $C_4$-alkyl group, a $C_5$- to $C_6$-cycloalkyl group, a phenyl group, methoxyphenyl group, a benzyl group, a phenylethyl group or a carboxyl group, R5 and R5' being equal or different from each other, and wherein Z denotes an oxygen or a group of formula $C(CN)_2$, C(CN)COOQ or $C(COOQ)_2$, wherein Q denotes a $C_1$- to $C_8$-alkyl group or an ethylene glycol mono($C_3$ to $C_7$)alkyl ether group, and L denotes said bridging group of said formula —[—CH═CH—]$_m$—CR═[═CH—CH═]$_n$═, wherein said R is said hydrogen, said phenyl group, said methyl group or said carboxamido group, and wherein m and n, independently of each other, are each 0, 1 or 2, with the proviso that n+m does not exceed 2.

5. The method as defined in claim 1, wherein said at least one monomethine or polymethine dye is selected from the group consisting of 4-(5-hydroxy-1,3-dimethyl-1H-pyrazol-4-ylmethylene)-2,5-dimethyl-2,4-dihydro-pyrazol-3-one,2-(2-hydroxyethyl)-4-(5-hydroxy-1-(2-hydroxyethyl)-3-methyl-1H-pyrazol-4-ylmethylene)-5-methyl-2,4-dihydropyrazol-3-one; 4-(5-hydroxy-3-methyl-1-(4-sulfophenyl)-1H-pyrazol-4-ylmethylene)-5-methyl-2-(4-sulfo-phenyl)-2,4-dihydropyrazol-3-one; diammonium 4-(5-hydroxy-3-methyl-1-(4-sulfophenyl)-1H-pyrazol-4-ylmethylene)-5-methyl-2-(4-sulfophenyl)-2,4-dihydropyrazol-3-one; 4-(3-(5-hydroxy-1,3-dimethyl-1H-pyrazol-4-yl)allylidene)-2,5-dimethyl-2,4-dihydropyrazol-3-one; 5-amino-4-(3-(3-amino-5-hydroxy-1-phenyl-1H-pyrazol-4-yl)allylidene)-2-phenyl-2,4-dihydropyrazol-3-one, 2-(2-hydroxyethyl)-4-(3-(5-hydroxy-1-(2-hydroxyethyl)-3-methyl-1H-pyrazol-4-yl)allylidene)-5-methyl-2,4-dihydropyrazol-3-one; 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; disodium 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; 4-(3-(5-hydroxy-3-methyl-1-(4-sulfophenyl)-1H-pyrazol-4-yl)-2-butenylidene)-5-methyl-2-(4-sulfophenyl)-2,4-dihydropyrazol-3-one; tripotassium 4-(3-(5-hydroxy-3-methyl-1-(4-sulfo-phenyl)-1H-pyrazol-4-yl)-2-butenylidene)-5-methyl-2-(4-sulfophenyl)-2,4-dihydropyrazol-3-one; 4-(3-(3-carboxy-5-oxo-1-(4-sulfophenyl)-1,5-dihydro-pyrazol-4-ylidene)propenyl)-5-hydroxy-1-(4-sulfophenyl)-1H-pyrazol-3-carboxylic acid; tetrasodium 4-(3-(3-carboxy-5-oxo-1-(4-sulfophenyl)-1,5-dihydropyrazol-4-ylidene)propenyl)-5-hydroxy-1-(4-sulfophenyl)-1H-pyrazol-3-carboxylic acid; 5-hydroxy-4-(3-(3-methoxycarbonyl-5-oxo-1-(4-sulfophenyl)-1,5-dihydropyrazol-4-ylidene)propenyl)-1-(4-sulfo-phenyl)-1H-pyrazol-3-carboxylic acid methyl ester; 4-(5-(5-hydroxy-1,3-dimethyl-1H-pyrazol-4-yl)penta-2,4-dienylidene)-2,5-dimethyl-2,4-dihydropyrazol-3-one, 5-amino-4-(5-(3-amino-5-hydroxy-1-phenyl-1H-pyrazol-4-yl)penta-2,4-dienylidene)-2-phenyl-2,4-di-hydropyrazol-3-one; 2-(2-hydroxyethyl)-4-(5-(5-hydroxy-1-(2-hydroxyethyl)-3-methyl-1H-pyrazol-4-yl)penta-2,4-dienylidene)-5-methyl-2,4-dihydro-pyrazol-3-one; 4-(5-(5-hydroxy-3-methyl-1-(4-sulfophenyl)-1H-pyrazol-4-yl)-penta-2,4-dienylidene)-5-methyl-2-(4-sulfophenyl)-2,4-dihydropyrazol-3-one; dipotassium 4-(5-(5-hydroxy-3-methyl-1-(4-sulfophenyl)-1H-pyrazol-4-yl )penta-2,4-dienylidene)-5-methyl-2-(4-sulfophenyl)-2,4-dihydropyrazol-3-one; 4-(5-(3-carboxy-5-oxo-1-(4-sulfo-phenyl)-1,5-dihydropyrazol-4-ylidene)penta-1,3-dienyl)-5-hydroxy-1-(4-sulfo-phenyl)-1H-pyrazol-3-carboxylic acid; dipotassium 4-(5-(3-carboxy-5-oxo-1-(4-sulfo-phenyl))-1,5-dihydropyrazol-4-ylidene)-penta-1,3-dienyl)-5-hydroxy-1-(4-sulfo-phenyl)-1H-pyrazole-3-carboxylic acid; 6-hydroxy-1-(2-hydroxyethyl)-5-(3-(1-(2-hydroxyethyl)-3-methyl-5-oxo-1,5-dihydropyrazol-4-ylidene)-propenyl)4-methyl-2-oxo-1,2-dihydropyridine-3-carbonitrile; 6-hydroxy-5-(3-(1-(2-hydroxy-ethyl-3-methyl-5-oxo-1,5-dihydropyrazol-4-ylidene)propenyl)-4-methyl-2-oxo-1-(4-sulfophenyl)-1,2-dihydropyridine-3-carbonitrile; potassium 6-hydroxy-5-(3-(1-(2-hydroxyethyl)-3-methyl-5-oxo-1,5-dihydropyrazol-4-ylidene)propenyl-4-methyl-2-oxo-1-(4-sulfophenyl)-1,2-dihydropyridine-3-carbonitrile; 6-hydroxy-4-methyl-5-(3-(3-methyl-5-oxo-1-(4-sulfophenyl)-1,5-dihydropyrazol-4-ylidene)-propenyl)-2-oxo-1-(4-sulfophenyl)-1,2-dihydropyridine-3-carbonitrile; dipotassium 6-hydroxy-4-methyl-5-(3-(3-methyl-5-oxo-1-(4-sulfophenyl)-1,5-dihydropyrazol-4-ylidene)-propenyl-2-oxo-1-(4-sulfophenyl)-1,2-dihydro-pyridine-3-carbonitrile; 6-hydroxy-4-methyl-5-(3-(3-methyl-5-oxo-1-phenyl-1,5-dihydropyrazole-4-ylidene)-propenyl)-2-oxo-1-(3-sulfophenyl)-1,2-dihydro-pyridine-3-carbonitrile; 4-(3-(5-cyano-2-hydroxy-4-methyl-6-oxo-1-phenyl-1,6-dihydropyridin-3-yl)allylidene)-5-oxo-1-(4-sulfophenyl)-4,5-dihydro-1H-pyrazole-3-carboxylic acid; 6-hydroxy-5-(3-(1-(2-hydroxyethyl)-3-methyl-5-oxo-1,5-dihydropyrazol-4-ylidene)propenyl)-4-methyl-2-oxo-1-phenyl-1,2-dihydro-pyridine-3-carbonitrile; 5-(3-(4-carboxy-2,6-dioxo-1,6-dihydro-2H-pyridin-3-ylidene)propenyl)-6-hydroxy-2-oxo-1,2-dihydro-pyridine-4-carboxylic acid; 2-(3-cyano-5-(3-(5-cyano-6-dicyanomethylene-4-methyl-2-oxo-1,6-dihydro-2H-pyridin-3-ylidene)propenyl)-6-hydroxy-4-methyl-1H-pyridin-2-ylidene)-malononitrile; 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile; triethylammonium-5-(3-(5-cyano-1-ethyl-4-methyl-2,6-dioxo-1,6-dihydro-2H-pyridin-3-ylidene)propenyl-1-ethyl-6-hydroxy-4-methyl-2-oxo-1,2-dihydropyridine-3-carbonitrile; 5-(3-(5-cyano-1-(2-hydroxyethyl)-4-methyl-2,6-dioxo-1,6-dihydro-2H-pyridin-3-ylidene)propenyl)-6-hydroxy-1-(2-hydroxyethyl)-4-methyl-2-oxo-1,2-dihydropyridine-3-carbonitrile; 5-(3-(5-cyano-1-ethyl-4-(4-methoxyphenyl)-2,6-dioxo-1,6-dihydro-2H-pyridin-3-ylidene)propenyl)-1-ethyl-6-hydroxy-4-(4- methoxyphenyl)-2-oxo-1 2-dihydro-pyridine-3-carbonitrile; 1-butyl-5-(3-(1-butyl-5-cyano-4-methyl-2,6-dioxo-1,6-dihydro-2H-pyridin-3-ylidene)propenyl)-6-hydroxy-4-methyl-2-oxo-1,2-dihydro-pyridine-3-carbonitrile; 5-(3-(5-cyano-1-(3-methoxypropyl)-4-methyl-2,6-dioxo-1,6-dihydro-2H-pyridin-3-ylidene)propenyl)-6-hydroxy-1-(3-methoxypropyl)-4-methyl-2-oxo-1,2-dihydropyridine-3-carbonitrile; 5-(3-(5-cyano-1-cyclohexyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile; 5-(3-(5-cyano-4-methyl-1-(2-morpholin-4-ylethyl)-2,6-dioxo-1,6-dihydro-2H-pyridin-3-ylidene)-propenyl)-6-hydroxy-4-methyl-1-(2-morpholin-4-ylethyl)-2-oxo-1 2-dihydro-pyridine-3-carbonitrile; 5-(3-(5-cyano-4-methyl-2,6-dioxo-1-(4-sulfophenyl)-1,6-dihydro-2H-pyridin-3-ylidene)propenyl)-6-hydroxy-4-methyl-2-oxo-1-(4-sulfo-phenyl)-1,2-dihydropyridine-3-carbonitrile; 5-(3-(5-cyano-4-methyl-2,6-dioxo-1-(3-sulfophenyl )-1,6-dihydro-2H-pyridin-3-ylidene)propenyl)-6-hydroxy-4-methyl-2-oxo-1-(3-sulfophenyl)-1,2-dihydropyridine-3-carbonitrile; 5-(3-(5-cyano-1-dimethylamino-4-methyl-2,6-dioxo-1,6-dihydro-2H-pyridin-3-ylidene)propenyl)-1-dimethylamino-6-hydroxy-4-methyl-2-oxo-1,2-dihydro-pyridine-3-carbonitrile; 5-(3-(5-carbamoyl-1-ethyl-4-methyl-2,6-dioxo-1,6-dihydro-2H-pyridin-3-ylidene)-propenyl)-1-ethyl-6-hydroxy-4-methyl-2-oxo-1,2-dihydropyridine-3-carboxamide, 1-ethyl-3-(3-(1-ethyl-2-hydroxy-5-methane-sulfonyl-4-methyl-6-oxo-1,6-dihydro-pyridin-3-yl)allylidene)-5-methanesulfonyl-4-methyl-3H-pyridino-2,6-dione and 5-(5-(5-cyano-1-ethyl-4-methyl-2,6-dioxo-1,6-dihydro-2H-pyridin-3-ylidene)-1,3-pentadienyl)-1-ethyl-6-hydroxy-4-methyl-2-oxo-1,2-dihydropyridine-3-carbonitrile.

6. The method as defined in claim 1, wherein said physiologically tolerated salt is selected from the group consisting of ammonium, sodium, potassium, N-methylmorpholinium, monoethanolammonium, diethanolammonium and triethanolammonium salts.

7. The method as defined in claim 1, wherein said colorant has a pH of from 2 to 11.

8. A method for coloring hair, said method comprising the steps of:
a) applying to the hair at least one polymer selected from the group consisting of natural polymers, synthetic polymers and modified polymers of natural origin and, in an amount sufficient for the coloring of the hair, a colorant, said colorant comprising at least one monomethine or polymethine dye of tautomeric formula (Ia/Ib), or a physiologically tolerated salt thereof, W=L–V'(Ia)⇌W'–L–V(Ib), wherein W=L–V' and W'=L–V are tautomers, and said W and said V each, independently of each other, is a substituted five-member or six-member heterocyclic ring, so that said W and W' are the same and said V and V' are the same, except that said W and said V each have a —C(=O)— group and said and said V' each have a =C(OH)— group in place of said —C(=O)— group in said substituted five-member or six-member heterocyclic ring, and wherein said substituted five-member or six-member heterocyclic ring for said W and for said V is each, independently of each other, selected from the group consisting of substituted pyrazolones, substituted pyridones, substituted dioxothiazolines, substituted rhodanines, substituted dioxoimidazolidines and substituted barbituric acid; and wherein L represents a bridging group of formula

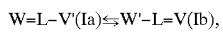
—[—CH=CH—]$_m$—CR=[=CH—CH=]$_n$—, wherein R is hydrogen, a phenyl group, a halogen atom, a methyl group or a carboxamido group, and wherein m and n, independently of each other, are each 0, 1 or 2, with the proviso that n+m does not exceed 2; and
b) styling the hair and subsequently drying the hair.

9. The method as defined in claim 8, wherein said at least one polymethine dye is a trimethine dye.

10. The method as defined in claim 8, wherein said at least one polymethine dye is a pentamethine dye.

11. The method as defined in claim 8, wherein said at least one monomethine or polymethine dye is selected from the group consisting of dye compounds of the formulas (II) to (IV):

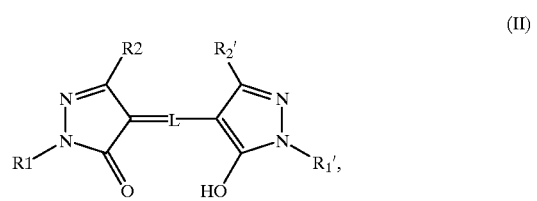

(II)

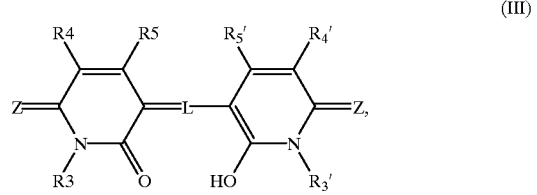

(III)

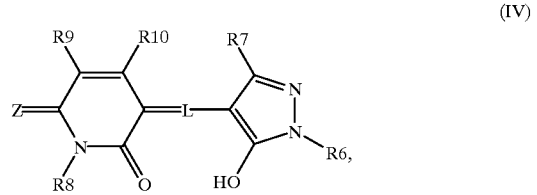

(IV)

wherein R1, R1' and R6 denote hydrogen; a straight-chain or branched $C_1$- to $C_8$-alkyl group; a hydroxyethyl group; a dihydroxypropyl group; a methoxyethyl group; a carboxyethyl group; a $C_1$- to $C_4$-sulfoalkyl group; a phenyl group; a substituted phenyl group substituted with one or more halogen atoms, with one or two sulfonic acid groups, with one or two carboxyl groups, with one or more straight-chain or branched $C_1$- to $C_8$-alkyl groups or with one or more $C_1$- to $C_8$-alkoxy groups; a benzyl group; a substitute benzyl group substituted with one or more halogen atoms, a $C_1$- to $C_4$-alkyl group, a hydroxy group, a methoxy group, a carboxyl group, a nitro group or an amino group or a five-member or six-member saturated or unsaturated heterocyclic ring; wherein R1 and R1' are equal or different from each other; and wherein R2, R2' and R7 denote hydrogen; a branched or straight chain $C_1$- to $C_6$-alkyl group; a phenyl group; an acylated phenyl group; a sulfonylated phenyl group; an amino group; an acylated amino group; a sulfonylated amino group; an acetyl group; a methoxy group; a carboxyl group; a carboxyl group esterified with a straight-chain or branched $C_1$- to $C_8$-alcohol, with ethylene glycol monomethyl ether or with ethylene glycol monoethyl ether; a carboxamido group; a carboxanilido group; a 2-amino-2-oxyethyl group or a nitrilo group, R2 and R2' being equal or different, and wherein R3, R3' and R8 denote hydrogen; a straight-chain or branched $C_1$- to $C_{11}$-alkyl group; a straight-chain or branched $C_1$- to $C_{11}$-monohydroxyalkyl group; a straight-chain or branched $C_1$- to $C_{11}$-dihydroxyalkyl group; a straight-chain or branched $C_1$- to $C_{11}$-alkoxyalkyl group; a straight-chain or branched $C_1$- to $C_{11}$-monoalkylamino group; an amino group of formula $(CH_2)_x$—NR11R12 wherein x is an integer from 0 to 3 and R11 and R12, independently of each other, denote an $C_1$- to $C_3$-alkyl group, a $C_2$- to $C_4$-sulfoalkyl group, a $C_2$- to $C_8$-carboxyalkyl group; a phenyl group; a substituted phenyl group having one or more halogen atoms, one or two sulfonic acid groups, one or more carboxyl groups, one or more straight-chain or branched $C_1$- to $C_8$-alkyl groups or one or more straight-chain or branched $C_1$- to $C_8$-alkoxy groups; a benzyl group; a substituted benzyl group having one or more halogen atoms, one or more $C_1$- to $C_4$-alkyl groups, a hydroxy group, a methoxy group, a nitro group or an amino group; a phenylethyl group; a five-member or six-member aromatic or nonaromatic heterocyclic group; a five-member or six-member aromatic or nonaromatic heterocyclic group attached by a methylene group; a pyrrolidino($C_1$- or $C_3$-)alkyl group; a morpholino($C_1$- or $C_3$-)alkyl group; a piperazino($C_1$- or $C_3$-)alkyl group; a piperidino($C_1$- or $C_3$-)alkyl group; a pyridino($C_1$- or $C_3$-)alkyl group or a trialkylammoniumalkyl group of formula R13—N(R14)$_3^+$ with R13 denoting a $C_1$- to $C_6$-alkylene group, R14 denoting a methyl or ethyl group and with a total number of carbon atoms being equal to 5 to 9, wherein R3 and R3' are equal or different from each other; and wherein R4, R4' and R9 denote hydrogen, a nitro group, a carboxylate ester group, a carboxamido group, a sulfonic acid group, a sulfomethyl group, a methanesulfonyl group, a pyridinium group or an imidazolium group, R4 and R4' being equal or different from each other; and wherein R5, R5' and R10 denote hydrogen, a $C_1$- to $C_4$-alkyl group, a $C_5$- to $C_6$-cycloalkyl group, a phenyl group, methoxyphenyl group, a benzyl group, a phenylethyl group or a carboxyl group, R5 and R5' being equal or different from each other, and wherein Z denotes an oxygen or a group of formula $C(CN)_2$, $C(CN)COOQ$ or $C(COOQ)_2$, wherein Q denotes a $C_1$- to $C_8$-alkyl group or an ethylene glycol mono($C_3$ to $C_7$)alkyl ether group, and L denotes said bridging group of said formula —[—CH=CH—]$_m$—CR=[=CH—CH=]$_n$=, wherein said R is said hydrogen, said phenyl group, said methyl group or said carboxamido group, and wherein m and n, independently of each other, are each 0, 1 or 2, with the proviso that n+m does not exceed 2.

12. The method as defined in claim 8, wherein said at least one monomethine or polymethine dye is selected from the group consisting of 4-(5-hydroxy-1,3-dimethyl-1H-pyrazol-4-ylmethylene)-2,5-dimethyl-2,4-dihydro-pyrazol-3-one,2-(2-hydroxyethyl)-4-(5-hydroxy-1-(2-hydroxyethyl)-3-methyl-1H-pyrazol-4-ylmethylene)-5-methyl-2,4-dihydropyrazol-3-one; 4-(5-hydroxy-3-methyl-1-(4-sulfophenyl)-1H-pyrazol-4-ylmethylene)-5-methyl-2-(4-sulfo-phenyl)-2,4-dihydropyrazol-3-one; diammonium 4-(5-hydroxy-3-methyl-1-(4-sulfophenyl)-1H-pyrazol-4-ylmethylene)-5-methyl-2-(4-sulfophenyl)-2,4-dihydropyrazol-3-one; 4-(3-(5-hydroxy-1,3-dimethyl-1H-pyrazol-4-yl)allylidene)-2,5-dimethyl-2,4-dihydropyrazol-3-one; 5-amino-4-(3-(3-amino-5-hydroxy-1-phenyl-1H-pyrazol-4-yl)allylidene)-2-phenyl-2,4-dihydropyrazol-3-one, 2-(2-hydroxyethyl)-4-(3-(5-hydroxy-1-(2-hydroxyethyl)-3-methyl-1H-pyrazol-4-yl)allylidene)-5-methyl-2,4-dihydropyrazol-3-one; 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; disodium 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; 4-(3-(5-hydroxy-3-methyl-1-(4-sulfophenyl)-1H-pyrazol-4-yl)-2-butenylidene)-5-methyl-2-(4-sulfophenyl)-2,4-dihydropyrazol-3-one; tripotassium 4-(3-(5-hydroxy-3-methyl-1-(4-sulfo-phenyl)-1H-pyrazol-4-yl)-2-butenylidene)-5-methyl-2-(4-sulfophenyl)-2,4-dihydropyrazol-3-one; 4-(3-(3-carboxy-5-oxo-1-(4-sulfophenyl)-1,5-dihydro-pyrazol-4-ylidene)propenyl)-5-hydroxy-1-(4-sulfophenyl)-1H-pyrazol-3-carboxylic acid; tetrasodium 4-(3-(3-carboxy-5-oxo-1-(4-sulfophenyl)-1,5-dihydropyrazol-4-ylidene)propenyl)-5-hydroxy-1-(4-sulfo-phenyl)-1H-pyrazol-3-carboxylic acid; 5-hydroxy-4-(3-(3-methoxycarbonyl-5-oxo-1-(4-sulfophenyl)-1,5-dihydropyrazol-4-ylidene)propenyl)-1-(4-sulfo-phenyl)-1H-pyrazol-3-carboxylic acid methyl ester; 4-(5-(5-hydroxy-1,3-dimethyl-1H-pyrazol-4-yl)penta-2,4-dienylidene)-2,5-dimethyl-2,4-dihydro-pyrazol-3-one, 5-amino-4-(5-(3-amino-5-hydroxy-1-phenyl-1H-pyrazol-4-yl)penta-2,4-dienylidene)-2-phenyl-2,4-di-hydropyrazol-3-one; 2-(2-hydroxy-ethyl)-4-(5-(5-hydroxy-1-(2-hydroxyethyl)-3-methyl-1H-pyrazol-4-yl)penta-2,4-dienylidene)-5-methyl -2,4-dihydro-pyrazol-3-one; 4-(5-(5-hydroxy-3-methyl-1-(4-sulfophenyl)-1H-pyrazol-4-yl)-penta-2,4-dienylidene)-5-methyl-2-(4-sulfo-phenyl)-2,4-dihydropyrazol-3-one; dipotassium 4-(5-(5-hydroxy-3-methyl-1-(4-sulfophenyl)-1H-pyrazol-4-yl)penta-2,4-dienylidene)-5-methyl-2-(4-sulfo-phenyl)-2,4-dihydropyrazol-3-one; 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazol-3-carboxylic acid; dipotassium 4-(5-(3-carboxy-5-oxo-1-(4-sulfo-phenyl))-1,5-dihydropyrazol-4-ylidene)-penta-1,3-dienyl)-5-hydroxy-1-(4-sulfo-phenyl)-1H-pyrazole-3-carboxylic acid; 6-hydroxy-1-(2-hydroxyethyl)-5-(3-(1-(2-hydroxyethyl)-3-methyl-5-oxo-1,5-dihydropyrazol-4-ylidene)-propenyl)-4-methyl-2-oxo-1,2-dihydropyridine-3-carbonitrile; 6-hydroxy-5-(3-(1-(2-hydroxyethyl-3-methyl-5-oxo-1,5-dihydropyrazol-4-ylidene)propenyl)-4-methyl-2-oxo-1-(4-sulfophenyl)-1,2-dihydropyridine-3-carbonitrile; potassium 6-hydroxy-5-(3-(1-(2-hydroxyethyl)-3-methyl-5-oxo-1,5-dihydropyrazol-4-ylidene)propenyl-4-methyl-2-oxo-1-(4-sulfophenyl)-1,2-dihydropyridine-3-carbonitrile; 6-hydroxy-4-methyl-5-(3-(3-methyl-5-oxo-1-(4-sulfophenyl)-1,5-dihydropyrazol-4-ylidene)propenyl)-2-oxo-1-(4-sulfophenyl)-1,2-dihydro-pyridine-3-carbonitrile; dipotassium 6-hydroxy-4-methyl-5-(3-(3-methyl-5-oxo-1-(4-sulfophenyl)-1,5-dihydropyrazol-4-ylidene)-propenyl-2-oxo-1-(4-sulfo-phenyl)-1,2-dihydropyridine-3-carbonitrile; 6-hydroxy-4-methyl-5-(3-(3-methyl-5-oxo-1-phenyl-1,5-dihydropyrazole-4-ylidene)-propenyl)-2-oxo-1-(3-sulfophenyl)-1,2-dihydropyridine-3-carbonitrile; 4-(3-(5-cyano-2-hydroxy-4-methyl-6-oxo-1-phenyl-1,6-dihydropyridin-3-yl)allylidene)-5-oxo-1-(4-sulfo-phenyl)-4,5-dihydro-1H-pyrazole-3-carboxylic acid; 6-hydroxy-5-(3-(1-(2-hydroxyethyl)-3-methyl-5-oxo-1,5-dihydropyrazol-4-ylidene)propenyl)-4-methyl-2-oxo-1-phenyl-1,2-dihydropyridine-3-carbonitrile; 5-(3-(4-carboxy-2,6-dioxo-1,6-dihydro-2H-pyridin-3-ylidene)propenyl)-6-hydroxy-2-oxo-1,2-dihydro-pyridine-4-carboxylic acid; 2-(3-cyano-5-(3-(5-cyano-6- dicyanomethylene-4-methyl-2-oxo-1,6-dihydro-2H-pyridin-3-ylidene)propenyl)-6-hydroxy-4-methyl-1H-pyridin-2-ylidene)-malononitrile; 5-(3-(5-cyano-1-ethyl-4-methyl-2,6-dioxo-1,6-dihydro-2H-pyridin-3-ylidene) propenyl)-1-ethyl-6-hydroxy-4-methyl-2-oxo-1,2-dihydropyridine-3-carbonitrile; triethylammonium-5-(3-(5-cyano-1-ethyl-4-methyl-2,6-dioxo-1,6-dihydro-2H-pyridin-3-ylidene)propenyl-1-ethyl-6-hydroxy-4-methyl-2-oxo-1,2-dihydropyridine-3-carbonitrile; 5-(3-(5-cyano-1-(2-hydroxy-ethyl)-4-methyl-2,6-dioxo-1,6-dihydro-2H-pyridin-3-ylidene)propenyl)-6-hydroxy-1-(2-hydroxyethyl)-4-methyl-2-oxo-1,2-dihydropyridine-3-carbonitrile; 5-(3-(5-cyano-1-ethyl-4-(4-methoxyphenyl)-2,6-dioxo-1,6-dihydro-2H-pyridin-3-ylidene)propenyl)-1-ethyl-6-hydroxy-4-(4-methoxyphenyl)-2-oxo-1,2-dihydropyridine-3-carbonitrile; 1-butyl-5-(3-(1-butyl-5-cyano-4-methyl-2,6-dioxo-1,6-dihydro-2H-pyridin-3-ylidene) propenyl)-6-hydroxy-4-methyl-2-oxo-1,2-dihydropyridine-3-carbonitrile; 5-(3-(5-cyano-1-(3-methoxypropyl)-4-methyl-2,6-dioxo-1,6-dihydro-2H-pyridin-3-ylidene)propenyl)-6-hydroxy-1-(3-methoxypropyl)-4-methyl-2-oxo-1,2-dihydropyridine-3-carbonitrile; 5-(3-(5-cyano-1-cyclohexyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile; 5-(3-(5-cyano-4-methyl-1-(2-morpholin-4-ylethyl)-2,6-dioxo-1,6-dihydro-2H-pyridin-3-ylidene)-propenyl)-6-hydroxy-4-methyl-1-(2-morpholin-4-ylethyl)-2-oxo-1,2-dihydro-pyridine-3-carbonitrile; 5-(3-(5-cyano-4-methyl-2,6-dioxo-1-(4-sulfophenyl)-1,6-dihydro-2H-pyridin-3-ylidene)propenyl)-6-hydroxy-4-methyl-2-oxo-1-(4-sulfo-phenyl)-1,2-dihydropyridine-3-carbonitrile; 5-(3-(5-cyano-4-methyl-2,6-dioxo-1-(3-sulfophenyl)-1,6-dihydro-2H-pyridin-3-ylidene)propenyl)-6-hydroxy-4-methyl-2-oxo-1-(3-sulfophenyl)-1,2-dihydropyridine-3-carbonitrile; 5-(3-(5-cyano-1-dimethylamino-4-methyl-2,6-dioxo-1,6-dihydro-2H-pyridin-3-ylidene)propenyl)-1-dimethylamino-6-hydroxy-4-methyl-2-oxo-1,2-dihydro-pyridine-3-carbonitrile; 5-(3-(5-carbamoyl-1-ethyl-4-methyl-2,6-dioxo-1,6-dihydro-2H-pyridin-3-ylidene)-propenyl)-1-ethyl-6-hydroxy-4-methyl-2-oxo-1,2-dihydropyridine-3-carboxamide, 1-ethyl-3-(3-(1-ethyl-2-hydroxy-5-methane-sulfonyl-4-methyl-6-oxo-1,6-dihydropyridin-3-yl)allylidene)-5-methanesulfonyl-4-methyl-3H-pyridino-2,6-dione and 5-(5-(5-cyano-1-ethyl-4-methyl-2,6-dioxo-1,6-dihydro-2H-pyridin-3-ylidene)-1,3-pentadienyl)-1-ethyl-6-hydroxy-4-methyl-2-oxo-1,2-dihydropyridine-3-carbonitrile.

13. The method as defined in claim 8, wherein said physiologically tolerated salt is selected from the group consisting of ammonium, sodium, potassium, N-methylmorpholinium, monoethanolammonium, diethanolammonium and triethanolammonium salts.

14. The method as defined in claim 8, wherein said colorant has a pH of from 2 to 11.

15. A method for temporarily coloring hair and subsequently decolorizing the hair after a predetermined time interval, said method comprising the steps of:
a) applying to the hair, in an amount sufficient for the coloring of the hair, a colorant, said colorant comprising at least one monomethine or polymethine dye of tautomeric formula (Ia/Ib), or a physiologically tolerated salt thereof,

wherein W=L–V' and W'=L–V are tautomers, and said W and said V each, independently of each other, is a substituted five-member or six-member heterocyclic ring, so that said W and W' are the same and said V and V' are the same, except that said W and said V each have a —C(=O)— group and said W' and said V' each have a =C(OH)— group in place of said —C(=C)— group in said substituted five-member or six-member heterocyclic ring, and wherein said substituted five-member or six-member heterocyclic ring for said W and for said V is each, independently of each other, selected from the group consisting of substituted pyrazolones, substituted pyridones, substituted dioxothiazolines, substituted rhodanines, substituted dioxoimidazolidines and substituted barbituric acid; and wherein L represents a bridging group of formula

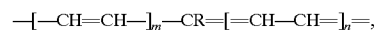

wherein R is hydrogen, a phenyl group, a halogen atom, a methyl group or a carboxamido group, and wherein m and n, independently of each other, are each 0, 1 or 2, with the proviso that n+m does not exceed 2;
b) after the applying of step a), allowing the colorant to act on the hair for a time interval of from 10 to 45 min at 20 to 50° C.;
c) rinsing the hair with water and subsequently drying the hair; and
d) at a later time after step c), decolorizing the hair with a reducing agent or an oxidant.

16. The method as defined in claim 15, further comprising, after the applying and the allowing, washing the hair with at least one of a shampoo and an aqueous solution of a weak organic acid and subsequently drying the hair.

17. The method as defined in claim 15, wherein said polymethine dye is a trimethine or a pentamethine dye.

18. The method as defined in claim 15, wherein said at least one monomethine or polymethine dye is selected from the group consisting of dye compounds of the formulas (II) to (IV):

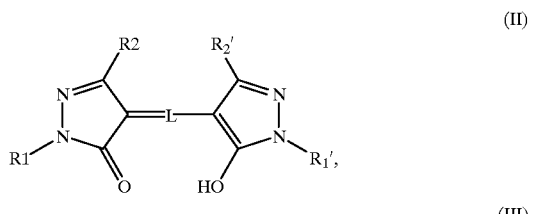

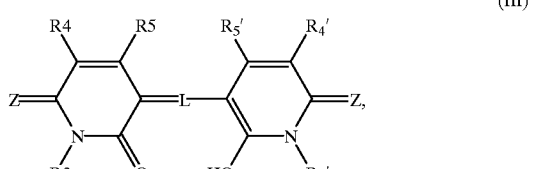

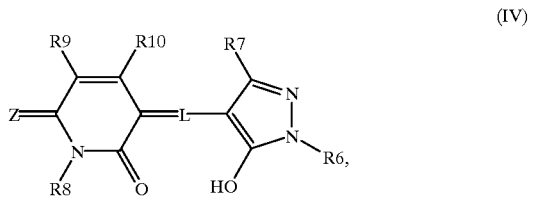

wherein R1, R1' and R6 denote hydrogen; a straight-chain or branched $C_1$- to $C_8$-alkyl group; a hydroxyethyl group; a dihydroxypropyl group; a methoxyethyl group; a carboxyethyl group; a $C_1$- to $C_4$-sulfoalkyl group; a phenyl group; a substituted phenyl group substituted with one or more halogen atoms, with one or two sulfonic acid groups, with one or two carboxyl groups, with one or more straight-chain or branched $C_1$- to $C_8$-alkyl groups or with one or more $C_1$- to $C_8$-alkoxy groups; a benzyl group; a substitute benzyl group substituted with one or more halogen atoms, a $C_1$- to $C_4$-alkyl group, a hydroxy group, a methoxy group, a carboxyl group, a nitro group or an amino group or a five-member or six-member saturated or unsaturated heterocyclic ring; wherein R1 and R1' are equal or different from each other; and wherein R2, R2' and R7 denote hydrogen; a branched or straight chain $C_1$- to $C_6$-alkyl group; a phenyl group; an acylated phenyl group; a sulfonylated phenyl group; an amino group; an acylated amino group; a sulfonylated amino group; an acetyl group; a methoxy group; a carboxyl group; a carboxyl group esterified with a straight-chain or branched $C_1$- to $C_8$-alcohol, with ethylene glycol monomethyl ether or with ethylene glycol monoethyl ether; a carboxamido group; a carboxanilido group; a 2-amino-2-oxyethyl group or a nitrilo group, R2 and R2' being equal or different, and wherein R3, R3' and R8 denote hydrogen; a straight-chain or branched $C_1$- to $C_{11}$-alkyl group; a straight-chain or branched $C_1$- to $C_{11}$-monohydroxyalkyl group; a straight-chain or branched $C_1$- to $C_{11}$-dihydroxyalkyl group; a straight-chain or branched $C_1$- to $C_{11}$-alkoxyalkyl group; a straight-chain or branched $C_1$- to $C_{11}$-monoalkylamino group; an amino group of formula $(CH_2)_x$—NR11R12 wherein x is an integer from 0 to 3 and R11 and R12, independently of each other, denote an $C_1$- to $C_3$-alkyl group, a $C_2$- to $C_4$-sulfoalkyl group, a $C_2$- to $C_8$-carboxyalkyl group; a phenyl group; a substituted phenyl group having one or more halogen atoms, one or two sulfonic acid groups, one or more carboxyl groups, one or more straight-chain or branched $C_1$- to $C_8$-alkyl groups or one or more straight-chain or branched $C_1$- to $C_8$-alkoxy groups; a benzyl group; a substituted benzyl group having one or more halogen atoms, one or more $C_1$- to $C_4$-alkyl groups, a hydroxy group, a methoxy group, a nitro group or an amino group; a phenylethyl group; a five-member or six-member aromatic or nonaromatic heterocyclic group; a five-member or six-member aromatic or nonaromatic heterocyclic group attached by a methylene group; a pyrrolidino($C_1$- or $C_3$-)alkyl group; a morpholino($C_1$- or $C_3$-)alkyl group; a piperazino($C_1$- or $C_3$-)alkyl group; a piperidino($C_1$- or $C_3$-)alkyl group; a pyridino($C_1$- or $C_3$-)alkyl group or a trialkylammoniumalkyl group of formula R13—N(R14)$_3^+$ with R13 denoting a $C_1$- to $C_6$-alkylene group, R14 denoting a methyl or ethyl group and with a total number of carbon atoms being equal to 5 to 9, wherein R3 and R3' are equal or different from each other; and wherein R4, R4' and R9 denote hydrogen, a nitro group, a carboxylate ester group, a carboxamido group, a sulfonic acid group, a sulfomethyl group, a methanesulfonyl group, a pyridinium group or an imidazolium group, R4 and R4' being equal or different from each other; and wherein R5, R5' and R10 denote hydrogen, a $C_1$- to $C_4$-alkyl group, a $C_5$- to $C_6$-cycloalkyl group, a phenyl group, methoxyphenyl group, a benzyl group, a phenylethyl group or a carboxyl group, R5 and R5' being equal or different from each other, and wherein Z denotes an oxygen or a group of formula $C(CN)_2$, $C(CN)COOQ$ or $C(COOQ)_2$, wherein Q denotes a $C_1$- to $C_8$-alkyl group or an ethylene glycol mono($C_3$ to $C_7$)alkyl ether group, and L denotes said bridging group of said formula —[—CH=CH—]$_m$—CR=[=CH—CH=]$_n$=, wherein said R is said hydrogen, said phenyl group, said methyl group or said carboxamido group, and wherein m and n, independently of each other, are each 0, 1 or 2, with the proviso that n+m does not exceed 2.

19. The method as defined in claim 15, wherein said at least one monomethine or polymethine dye is selected from the group consisting of 4-(5-hydroxy-1,3-dimethyl-1H-pyrazol-4-ylmethylene)-2,5-dimethyl-2,4-dihydro-pyrazol-3-one, 2-(2-hydroxyethyl)-4-(5-hydroxy-1-(2-hydroxyethyl)-3-methyl-1H-pyrazol-4-ylmethylene)-5-methyl-2,4-dihydropyrazol-3-one; 4-(5-hydroxy-3-methyl-1-(4-sulfophenyl)-1H-pyrazol-4-ylmethylene)-5-methyl-2-(4-sulfo-phenyl)-2,4-dihydropyrazol-3-one; diammonium 4-(5-hydroxy-3-methyl-1-(4-sulfophenyl)-1H-pyrazol-4-ylmethylene)-5-methyl-2-(4-sulfophenyl)-2,4-dihydropyrazol-3-one; 4-(3-(5-hydroxy-1,3-dimethyl-1H-pyrazol-4-yl)allylidene)-2,5-dimethyl-2,4-dihydropyrazol-3-one; 5-amino-4-(3-(3-amino-5-hydroxy-1-phenyl-1H-pyrazol-4-yl)allylidene)-2-phenyl-2,4-dihydropyrazol-3-one, 2-(2-hydroxyethyl)-4-(3-(5-hydroxy-1-(2-hydroxyethyl)-3-methyl-1H-pyrazol-4-yl)allylidene)-5-methyl-2,4-dihydropyrazol-3-one; 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; disodium 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; 4-(3-(5-hydroxy-3-methyl-1-(4-sulfophenyl)-1H-pyrazol-4-yl)-2-butenylidene)-5-methyl-2-(4-sulfophenyl)-2,4-dihydropyrazol-3-one; tripotassium 4-(3-(5-hydroxy-3-methyl-1-(4-sulfo-phenyl)-1H-pyrazol-4-yl)-2-butenylidene)-5-methyl-2-(4-sulfophenyl)-2,4-dihydropyrazol-3-one; 4-(3-(3-carboxy-5-oxo-1-(4-sulfophenyl)-1,5-dihydro-pyrazol-4-ylidene)propenyl)-5-hydroxy-1-(4-sulfo-phenyl)-1H-pyrazol-3-carboxylic acid; tetrasodium 4-(3-(3-carboxy-5-oxo-1-(4-sulfophenyl)-1,5-dihydropyrazol-4-ylidene)propenyl)-5-hydroxy-1-(4-sulfophenyl)-1H-pyrazol-3-carboxylic acid; 5-hydroxy-4-(3-(3-methoxycarbonyl-5-oxo-1-(4-sulfophenyl)-1,5-dihydropyrazol-4-ylidene)propenyl)-1-(4-sulfo-phenyl)-1H-pyrazol-3-carboxylic acid methyl ester; 4-(5-(5-hydroxy-1,3-dimethyl-1H-pyrazol-4-yl)penta-2,4-dienylidene)-2,5-dimethyl-2,4-dihydro-pyrazol-3-one, 5-amino-4-(5-(3-amino-5-hydroxy-1-phenyl-1H-pyrazol-4-yl)-penta-2,4-dienylidene)-2-phenyl-2,4-di-hydropyrazol-3-one; 2-(2-hydroxyethyl)-4-(5-(5-hydroxy-1-(2-hydroxyethyl)-3-methyl-1H-pyrazol-4-yl)penta-2,4-dienylidene)-5-methyl-2,4-dihydro-pyrazol-3-one; 4-(5-(5-hydroxy-3-methyl-1-(4-sulfophenyl)-1H-pyrazol-4-yl)-penta-2,4-dienylidene)-5-methyl-2-(4-sulfo-phenyl)-2,4-dihydropyrazol-3-one; dipotassium 4-(5-(5-hydroxy-3-methyl-1-(4-sulfophenyl)-1H-pyrazol-4-yl)penta-2,4-dienylidene)-5-methyl-2-(4-sulfo-phenyl)-2,4-dihydropyrazol-3-one; 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazol-3-carboxylic acid; dipotassium 4-(5-(3-carboxy-5-oxo-1-(4-sulfo-phenyl))-1,5-dihydropyrazol-4-ylidene)-penta-1,3-dienyl)-5-hydroxy-1-(4-sulfo-phenyl)-1H-pyrazole-3-carboxylic acid; 6-hydroxy-1-(2-hydroxyethyl)-5-(3-(1-(2-hydroxyethyl)-3-methyl-5-oxo-1,5-dihydropyrazol-4-ylidene)-propenyl)-4-methyl-2-oxo-1,2-dihydropyridine-3- carbonitrile; 6-hydroxy-5-(3-(1-(2-hydroxyethyl-3-methyl-5-oxo-1,5-dihydropyrazol-4-ylidene)propenyl)-4-methyl-2-oxo-1-(4-sulfophenyl)-1,2-dihydropyridine-3-carbonitrile; potassium 6-hydroxy-5-(3-(1-(2-hydroxyethyl)-3-methyl-5-oxo-1,5-dihydropyrazol-4-ylidene)propenyl-4-methyl-2-oxo-1-(4-sulfophenyl)-1,2-dihydropyridine-3-carbonitrile; 6-hydroxy-4-methyl-5-(3-(3-methyl-5-oxo-1-(4-sulfophenyl)-1,5-dihydropyrazol-4-ylidene)propenyl)-2-oxo-1-(4-sulfophenyl)-1,2-dihydro-pyridine-3-carbonitrile; dipotassium 6-hydroxy-4-methyl-5-(3-(3-methyl-5-oxo-1-(4-sulfophenyl)-1,5-dihydropyrazol-4-ylidene)-propenyl-2-oxo-1-(4-sulfo-phenyl)-1,2-dihydropyridine-3-carbonitrile; 6-hydroxy-4-methyl-5-(3-(3-methyl-5-oxo-1-phenyl-1,5-dihydropyrazole-4-ylidene)-propenyl)-2-oxo-1-(3-sulfo-phenyl)-1,2-dihydropyridine-3-carbonitrile; 4-(3-(5-cyano-2-hydroxy-4-methyl-6-oxo-1-phenyl-1,6-dihydropyridin-3-yl)allylidene)-5-oxo-1-(4-sulfophenyl)-4,5-dihydro-1H-pyrazole-3-carboxylic acid; 6-hydroxy-5-(3-(1-(2-hydroxyethyl)-3-methyl-5-oxo-1,5-dihydropyrazol-4-ylidene)propenyl)-4-methyl-2-oxo-1-phenyl-1,2-dihydropyridine-3-carbonitrile; 5-(3-(4-carboxy-2,6-dioxo-1,6-dihydro-2H-pyridin-3-ylidene)propenyl)-6-hydroxy-2-oxo-1,2-dihydro-pyridine-4-carboxylic acid; 2-(3-cyano-5-(3-(5-cyano-6-dicyanomethylene-4-methyl-2-oxo-1,6-dihydro-2H-pyridin-3-ylidene)propenyl)-6-hydroxy-4-methyl-1H-pyridin-2-ylidene)-malononitrile; 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile; triethylammonium-5-(3-(5-cyano-1-ethyl-4-methyl-2,6-dioxo-1,6-dihydro-2H-pyridin-3-ylidene)propenyl-1-ethyl-6-hydroxy-4-methyl-2-oxo-1,2-dihydropyridine-3-carbonitrile; 5-(3-(5-cyano-1-(2-hydroxyethyl)-4-methyl-2,6-dioxo-1,6-dihydro-2H-pyridin-3-ylidene)propenyl)-6-hydroxy-1-(2-hydroxyethyl)-4-methyl-2-oxo-1,2-dihydropyridine-3-carbonitrile; 5-(3-(5-cyano-1-ethyl-4-(4-methoxyphenyl)-2,6-dioxo-1,6-dihydro-2H-pyridin-3-ylidene)propenyl)-1-ethyl-6-hydroxy-4-(4-methoxyphenyl)-2-oxo-1,2-dihydro-pyridine-3-carbonitrile; 1-butyl-5-(3-(1-butyl-5-cyano-4-methyl-2,6-dioxo-1,6-dihydro-2H-pyridin-3-ylidene)propenyl)-6-hydroxy-4-methyl-2-oxo-1,2-dihydro-pyridine-3-carbonitrile; 5-(3-(5-cyano-1-(3-methoxypropyl)-4-methyl-2,6-dioxo-1,6-dihydro-2H-pyridin-3-ylidene)propenyl)-6-hydroxy-1-(3-methoxypropyl)-4-methyl-2-oxo-1,2-dihydropyridine-3-carbonitrile; 5-(3-(5-cyano-1-cyclohexyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile; 5-(3-(5-cyano-4-methyl-1-(2-morpholin-4-ylethyl)-2,6-dioxo-1,6-dihydro-2H-pyridin-3-ylidene)-propenyl)-6-hydroxy-4-methyl-1-(2-morpholin-4-ylethyl)-2-oxo-1,2-dihydro-pyridine-3-carbonitrile; 5-(3-(5-cyano-4-methyl-2,6-dioxo-1-(4-sulfophenyl)-1,6-dihydro-2H-pyridin-3-ylidene)propenyl)-6-hydroxy-4-methyl-2-oxo-1-(4-sulfo-phenyl)-1,2-dihydropyridine-3-carbonitrile; 5-(3-(5-cyano-4-methyl-2,6-dioxo-1-(3-sulfophenyl)-1,6-dihydro-2H-pyridin-3-ylidene)propenyl)-6-hydroxy-4-methyl-2-oxo-1-(3-sulfophenyl)-1,2-dihydropyridine-3-carbonitrile; 5-(3-(5-cyano-1-dimethylamino-4-methyl-2,6-dioxo-1,6-dihydro-2H-pyridin-3-ylidene)propenyl)-1-dimethylamino-6-hydroxy-4-methyl-2-oxo-1,2-dihydropyridine-3-carbonitrile; 5-(3-(5-carbamoyl-1-ethyl-4-methyl-2,6-dioxo-1,6-dihydro-2H-pyridin-3-ylidene)-propenyl)-1-ethyl-6-hydroxy-4-methyl-2-oxo-1,2-dihydropyridine-3-carboxamide, 1-ethyl-3-(3-(1-ethyl-2-hydroxy-5-methane-sulfonyl-4-methyl6-oxo-1,6-dihydropyridin-3-yl)allylidene)-5-methanesulfonyl-4-methyl-3H-pyridino-2,6-dione and 5-(5-(5-cyano-1-ethyl-4-methyl-2,6-dioxo-1,6-dihydro-2H-pyridin-3-ylidene)-1,3-pentadienyl)-1-ethyl-6-hydroxy-4-methyl-2-oxo-1,2-dihydropyridine-3-carbonitrile.

20. The method as defined in claim 15, wherein said physiologically tolerated salt is selected from the group consisting of ammonium, sodium, potassium, N-methylmorpholinium, monoethanolammonium, diethanolammonium and triethanolammonium salts.

21. The method as defined in claim 15, wherein said colorant has a pH of from 2 to 11.

22. The method as defined in claim 15, wherein the reducing agent is an alkali metal sulfite, an alkali metal hydrogen sulfite, an alkali metal metabisulfite, an ammonium sulfite or an ammonium hydrogen sulfite.

23. The method as defined in claim 15, wherein the reducing agent is a combination of an alkali metal sulfite, an alkali metal hydrogen sulfite, an alkali metal metabisulfite, an ammonium sulfite or an ammonium hydrogen sulfite with at least one member selected from the group consisting of reductones and thiols.

24. The method as defined in claim 15, wherein the oxidant is a bleaching powder containing from 5 to 50 percent by weight of a persulfate compound selected from the group consisting of alkali metal persulfates and ammonium persulfates.

25. The method as defined in claim 15, wherein the oxidant is a hydrogen peroxide solution in combination with a bleaching powder containing from 5 to 50 percent by weight of a persulfate compound selected from the group consisting of alkali metal persulfates and ammonium persulfates.

26. A method for temporarily coloring hair and subsequently decolorizing the hair after a predetermined time interval, said method comprising the steps of:

a) applying to the hair at least one polymer selected from the group consisting of synthetic polymers, natural polymers and modified polymers of natural origin and, in an amount sufficient for the coloring of the hair, a colorant, said colorant comprising at least one monomethine or polymethine dye of tautomeric formula (Ia/Ib), or a physiologically tolerated salt thereof, $$W=L-V'(Ia) \rightleftharpoons W'-L=V(Ib),$$

wherein W=L–V' and W'=L–V are tautomers, and said W and said V each, independently of each other, is a substituted five-member or six-member heterocyclic ring, so that said W and W' are the same and said V and V' are the same, except that said W and said V each have a —C(=C)— group and said W' and said V' each have a =C(OH)— group in place of said —C(=C)— group in said substituted five-member or six-member heterocyclic ring, and wherein said substituted five-member or six-member heterocyclic ring for said W and for said V is each, independently of each other, selected from the group consisting of substituted pyrazolones, substituted pyridones, substituted dioxothiazolines, substituted rhodanines, substituted dioxoimidazolidines and substituted barbituric acid; and wherein L represents a bridging group of formula $$-[-CH=CH-]_m-CR=[=CH-CH=]_n-,$$

wherein R is hydrogen, a phenyl group, a halogen atom, a methyl group or a carboxamido group, and wherein m and n, independently of each other, are each 0, 1 or 2, with the proviso that n+m does not exceed 2;

b) styling the hair and subsequently drying the hair; and
c) at a later time after step b), decolorizing the hair with a reducing agent or an oxidant.

27. The method as defined in claim 26, wherein said polymethine dye is a trimethine dye.

28. The method as defined in claim 26, wherein said polymethine dye is a pentamethine dye.

29. The method as defined in claim 26, wherein said at least one monomethine or polymethine dye is selected from the group consisting of dye compounds of the formulas (II) to (IV):

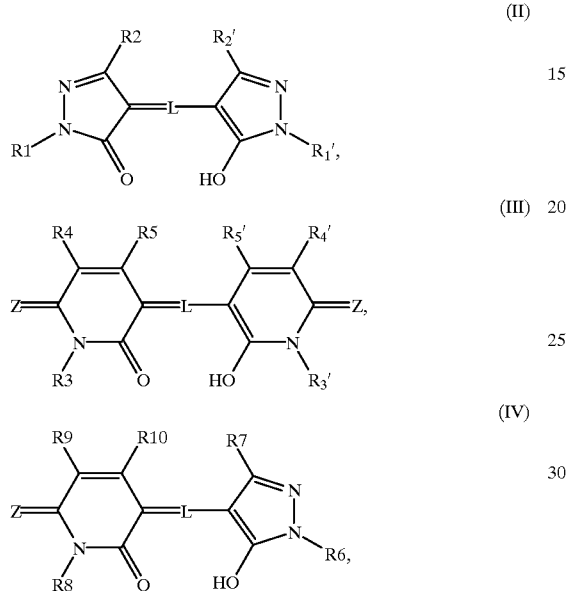

wherein R1, R1' and R6 denote hydrogen; a straight-chain or branched $C_1$- to $C_8$-alkyl group; a hydroxyethyl group; a dihydroxypropyl group; a methoxyethyl group; a carboxyethyl group; a $C_1$- to $C_4$-sulfoalkyl group; a phenyl group; a substituted phenyl group substituted with one or more halogen atoms, with one or two sulfonic acid groups, with one or two carboxyl groups, with one or more straight-chain or branched $C_1$- to $C_8$-alkyl groups or with one or more $C_1$- to $C_8$-alkoxy groups; a benzyl group; a substitute benzyl group substituted with one or more halogen atoms, a $C_1$- to $C_4$-alkyl group, a hydroxy group, a methoxy group, a carboxyl group, a nitro group or an amino group or a five-member or six-member saturated or unsaturated heterocyclic ring; wherein R1 and R1' are equal or different from each other; and wherein R2, R2' and R7 denote hydrogen; a branched or straight chain $C_1$- to $C_6$-alkyl group; a phenyl group; an acylated phenyl group; a sulfonylated phenyl group; an amino group; an acylated amino group; a sulfonylated amino group; an acetyl group; a methoxy group; a carboxyl group; a carboxyl group esterified with a straight-chain or branched $C_1$- to $C_8$-alcohol, with ethylene glycol monomethyl ether or with ethylene glycol monoethyl ether; a carboxamido group; a carboxanilido group; a 2-amino-2-oxyethyl group or a nitrilo group, R2 and R2' being equal or different, and wherein R3, R3' and R8 denote hydrogen; a straight-chain or branched $C_1$- to $C_{11}$-alkyl group; a straight-chain or branched $C_1$- to $C_{11}$-monohydroxyalkyl group; a straight-chain or branched $C_1$- to $C_{11}$-dihydroxyalkyl group; a straight-chain or branched $C_1$- to $C_{11}$-alkoxyalkyl group; a straight-chain or branched $C_1$- to $C_{11}$-monoalkylamino group; an amino group of formula $(CH_2)_x$—NR11R12 wherein x is an integer from 0 to 3 and R11 and R12, independently of each other, denote an $C_1$- to $C_3$-alkyl group, a $C_2$- to $C_4$-sulfoalkyl group, a $C_2$- to $C_8$-carboxyalkyl group; a phenyl group; a substituted phenyl group having one or more halogen atoms, one or two sulfonic acid groups, one or more carboxyl groups, one or more straight-chain or branched $C_1$- to $C_8$-alkyl groups or one or more straight-chain or branched $C_1$- to $C_8$-alkoxy groups; a benzyl group; a substituted benzyl group having one or more halogen atoms, one or more $C_1$- to $C_4$-alkyl groups, a hydroxy group, a methoxy group, a nitro group or an amino group; a phenylethyl group; a five-member or six-member aromatic or nonaromatic heterocyclic group; a five-member or six-member aromatic or nonaromatic heterocyclic group attached by a methylene group; a pyrrolidino($C_1$- or $C_3$-)alkyl group; a morpholino($C_1$- or $C_3$-)alkyl group; a piperazino($C_1$- or $C_3$-)alkyl group; a piperidino($C_1$- or $C_3$-)alkyl group; a pyridino($C_1$- or $C_3$-)alkyl group or a trialkylammoniumalkyl group of formula R13—N(R14)$_3^+$ with R13 denoting a $C_1$- to $C_6$-alkylene group, R14 denoting a methyl or ethyl group and with a total number of carbon atoms being equal to 5 to 9, wherein R3 and R3' are equal or different from each other; and wherein R4, R4' and R9 denote hydrogen, a nitro group, a carboxylate ester group, a carboxamido group, a sulfonic acid group, a sulfomethyl group, a methanesulfonyl group, a pyridinium group or an imidazolium group, R4 and R4' being equal or different from each other; and wherein R5, R5' and R10 denote hydrogen, a $C_1$- to $C_4$-alkyl group, a $C_5$- to $C_6$-cycloalkyl group, a phenyl group, methoxyphenyl group, a benzyl group, a phenylethyl group or a carboxyl group, R5 and R5' being equal or different from each other, and wherein Z denotes an oxygen or a group of formula $C(CN)_2, C(CN)COOQ$ or $C(COOQ)_2$, wherein Q denotes a $C_1$- to $C_8$-alkyl group or an ethylene glycol mono($C_3$ to $C_7$)alkyl ether group, and L denotes said bridging group of said formula —[—CH=CH—]$_m$—CR=[=CH—CH=]$_n$=, wherein said R is said hydrogen, said phenyl group, said methyl group or said carboxamido group, and wherein m and n, independently of each other, are each 0, 1 or 2, with the proviso that n+m does not exceed 2.

30. The method as defined in claim 26, wherein said at least one monomethine or polymethine dye is selected from the group consisting of 4-(5-hydroxy-1,3-dimethyl-1H-pyrazol4-ylmethylene)-2, 5-dimethyl-2,4-dihydro-pyrazol-3-one,2-(2-hydroxyethyl)-4-(5-hydroxy-1-(2-hydroxyethyl)-3-methyl-1H-pyrazol-4-ylmethylene)-5-methyl-2,4-dihydropyrazol-3-one; 4-(5-hydroxy-3-methyl-1-(4-sulfophenyl)-1H-pyrazol-4-ylmethylene)-5-methyl-2-(4-sulfo-phenyl)-2,4-dihydropyrazol-3-one; diammonium 4-(5-hydroxy-3-methyl-1-(4-sulfophenyl)-1H-pyrazol-4-ylmethylene)-5-methyl-2-(4-sulfophenyl)-2,4-dihydropyrazol-3-one; 4-(3-(5-hydroxy-1,3-dimethyl-1H-pyrazol-4-yl)allylidene)-2,5-dimethyl-2,4-dihydropyrazol-3-one; 5-amino-4-(3-(3-amino-5-hydroxy-1-phenyl-1H-pyrazol-4-yl)allylidene)-2-phenyl-2,4-dihydropyrazol-3-one, 2-(2-hydroxyethyl)-4-(3-(5-hydroxy-1-(2-hydroxyethyl)-3-methyl-1H-pyrazol-4-yl)allylidene)-5-methyl-2,4-dihydropyrazol-3-one; 4-(3-(5-hydroxy-3- methyl-1-(4-sulfophenyl)-1H-pyrazol-4-yl)allylidene)-5-methyl-2-(4-sulfophenyl)-2,4-dihydropyrazol-3-one; disodium 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; 4-(3-(5-hydroxy-3-methyl-1-(4-sulfophenyl)-1H-pyrazol-4-yl)-2-butenylidene)-5-methyl-2-(4-sulfophenyl)-2,4-dihydropyrazol-3-one; tripotassium 4-(3-(5-hydroxy-3-methyl-1-(4-sulfo-phenyl)-1H-pyrazol-4-yl )-2-butenylidene)-5-methyl-2-(4-sulfophenyl)-2,4-dihydropyrazol-3-one; 4-(3-(3-carboxy-5-oxo-1-(4-sulfophenyl)-1,5-dihydro-pyrazol-4-ylidene)propenyl)-5-hydroxy-1-(4-sulfo-phenyl)-1H-pyrazol-3-carboxylic acid; tetrasodium 4-(3-(3-carboxy-5-oxo-1-(4-sulfophenyl)-1,5-dihydropyrazol-4-ylidene)propenyl)-5-hydroxy-1-(4-sulfophenyl)-1H-pyrazol-3-carboxylic acid; 5-hydroxy-4-(3-(3-methoxycarbonyl-5-oxo-1-(4-sulfophenyl)-1,5-dihydropyrazol-4-ylidene)propenyl)-1-(4-sulfo-phenyl)-1H-pyrazol-3-carboxylic acid methyl ester; 4-(5-(5-hydroxy-1,3-dimethyl-1H-pyrazol-4-yl)penta-2,4-dienylidene)-2,5-dimethyl-2,4-dihydropyrazol-3-one, 5-amino-4-(5-(3-amino-5-hydroxy-1-phenyl-1H-pyrazol-4-yl)penta-2,4-dienylidene)-2-phenyl-2,4-di-hydropyrazol-3-one; 2-(2-hydroxyethyl)-4-(5-(5-hydroxy-1-(2-hydroxyethyl)-3-methyl-1H-pyrazol-4-yl)penta-2,4-dienylidene)-5-methyl-2,4-dihydro-pyrazol-3-one; 4-(5-(5-hydroxy-3-methyl-1-(4-sulfophenyl)-1H-pyrazol-4-yl)-penta-2,4-dienylidene)-5-methyl-2-(4-sulfophenyl)-2,4-dihydropyrazol-3-one; dipotassium 4-(5-(5-hydroxy-3-methyl-1-(4-sulfophenyl)-1H-pyrazol-4-yl)penta-2,4-dienylidene)-5-methyl-2-(4-sulfophenyl)-2,4-dihydropyrazol-3-one; 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazol-3-carboxylic acid; dipotassium 4-(5-(3-carboxy-5-oxo-1-(4-sulfo-phenyl))-1,5-dihydropyrazol-4-ylidene)-penta-1,3-dienyl)-5-hydroxy-1-(4-sulfo-phenyl)-1H-pyrazole-3-carboxylic acid; 6-hydroxy-1-(2-hydroxyethyl)-5-(3-(1-(2-hydroxyethyl)-3-methyl-5-oxo-1,5-dihydropyrazol-4-ylidene)-propenyl)-4-methyl-2-oxo-1,2-dihydropyridine-3-carbonitrile; 6-hydroxy-5-(3-(1-(2-hydroxyethyl-3-methyl-5-oxo-1,5-dihydropyrazol-4-ylidene)propenyl)-4-methyl-2-oxo-1-(4-sulfophenyl)-1,2-dihydropyridine-3-carbonitrile; potassium 6-hydroxy-5-(3-(1-(2-hydroxyethyl)-3-methyl-5-oxo-1,5-dihydropyrazol-4-ylidene)-propenyl-4-methyl-2-oxo-1-(4-sulfophenyl)-1,2-dihydropyridine-3-carbonitrile; 6-hydroxy-4-methyl-5-(3-(3-methyl-5-oxo-1-(4-sulfophenyl)-1,5-dihydropyrazol-4-ylidene)propenyl)-2-oxo-1-(4-sulfophenyl)-1,2-dihydropyridine-3-carbonitrile; dipotassium 6-hydroxy-4-methyl-5-(3-(3-methyl-5-oxo-1-(4-sulfophenyl)-1,5-dihydropyrazol-4-ylidene)-propenyl-2-oxo-1-(4-sulfophenyl)-1,2-dihydro-pyridine-3-carbonitrile; 6-hydroxy-4-methyl-5-(3-(3-methyl-5-oxo-1-phenyl-1,5-dihydropyrazole-4-ylidene)-propenyl)-2-oxo-1-(3-sulfophenyl)-1,2-dihydro-pyridine-3-carbonitrile; 4-(3-(5-cyano-2-hydroxy-4-methyl-6-oxo-1-phenyl-1,6-dihydropyridin-3-yl)allylidene)-5-oxo-1-(4-sulfophenyl)-4,5-dihydro-1H-pyrazole-3-carboxylic acid; 6-hydroxy-5-(3-(1-(2-hydroxyethyl)-3-methyl-5-oxo-1,5-dihydropyrazol-4-ylidene)propenyl)-4-methyl-2-oxo-1-phenyl-1,2-dihydropyridine-3-carbonitrile; 5-(3-(4-carboxy-2,6-dioxo-1,6-dihydro-2H-pyridin-3-ylidene)propenyl)-6-hydroxy-2-oxo-1,2-dihydro-pyridine-4-carboxylic acid; 2-(3-cyano-5-(3-(5-cyano-6-dicyanomethylene-4-methyl-2-oxo-1,6-dihydro-2H-pyridin-3-ylidene)propenyl)-6-hydroxy4-methyl-1H-pyridin-2-ylidene)-malononitrile; 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile; triethylammonium-5-(3-(5-cyano-1-ethyl-4-methyl-2,6-dioxo-1,6-dihydro-2H-pyridin-3-ylidene)propenyl-1-ethyl-6-hydroxy-4-methyl-2-oxo-1,2-dihydropyridine-3-carbonitrile; 5-(3-(5-cyano-1-(2-hydroxyethyl)-4-methyl-2,6-dioxo-1,6-dihydro-2H-pyridin-3-ylidene)propenyl)-6-hydroxy-1-(2-hydroxyethyl)-4-methyl-2-oxo-1,2-dihydropyridine-3-carbonitrile; 5-(3-(5-cyano-1-ethyl-4-(4-methoxyphenyl)-2,6-dioxo-1,6-dihydro-2H-pyridin-3-ylidene)propenyl)-1-ethyl-6-hydroxy4-(4-methoxyphenyl)-2-oxo-1,2-dihydro-pyridine-3-carbonitrile; 1-butyl-5-(3-(1-butyl-5-cyano-4-methyl-2,6-dioxo-1,6-dihydro-2H-pyridin-3-ylidene)propenyl)-6-hydroxy-4-methyl-2-oxo-1,2-dihydro-pyridine-3-carbonitrile; 5-(3-(5-cyano-1-(3-methoxypropyl)-4-methyl-2,6-dioxo-1,6-dihydro-2H-pyridin-3-ylidene)propenyl)-6-hydroxy-1-(3-methoxypropyl)-4-methyl-2-oxo-1,2-dihydropyridine-3-carbonitrile; 5-(3-(5-cyano-1-cyclohexyl-4-methyl-2,6-dioxo-1,6-dihydro-2H-pyridin-3-ylidene)propenyl)-1-ethyl-6-hydroxy-4-methyl-2-oxo-1,2-dihydro-pyridine-3-carbonitrile; 5-(3-(5-cyano-4-methyl-1-(2-morpholin-4-ylethyl)-2,6-dioxo-1,6-dihydro-2H-pyridin-3-ylidene)-propenyl)-6-hydroxy-4-methyl-1-(2-morpholin-4-ylethyl)-2-oxo-1,2-dihydro-pyridine-3-carbonitrile; 5-(3-(5-cyano-4-methyl-2,6-dioxo-1-(4-sulfophenyl)-1,6-dihydro-2H-pyridin-3-ylidene)propenyl)-6-hydroxy-4-methyl-2-oxo-1-(4-sulfo-phenyl)-1,2-dihydropyridine-3-carbonitrile; 5-(3-(5-cyano-4-methyl-2,6-dioxo-1-(3-sulfophenyl)-1,6-dihydro-2H-pyridin-3-ylidene)propenyl)-6-hydroxy-4-methyl-2-oxo-1-(3-sulfophenyl)-1,2-dihydropyridine-3-carbonitrile; 5-(3-(5-cyano-1-dimethylamino-4-methyl-2,6-dioxo-1,6-dihydro-2H-pyridin-3-ylidene)propenyl)-1-dimethylamino-6-hydroxy-4-methyl-2-oxo-1,2-dihydro-pyridine-3-carbonitrile; 5-(3-(5-carbamoyl-1-ethyl-4-methyl-2,6-dioxo-1,6-dihydro-2H-pyridin-3-ylidene)-propenyl)-1-ethyl-6-hydroxy-4-methyl-2-oxo-1,2-dihydropyridine-3-carboxamide, 1-ethyl-3-(3-(1-ethyl-2-hydroxy-5-methane-sulfonyl-4-methyl-6-oxo-1,6-dihydropyridin-3-yl)allylidene)-5-methanesulfonyl-4-methyl-3H-pyridino-2,6-dione and 5-(5-(5-cyano-1-ethyl-4-methyl-2,6-dioxo-1,6-dihydro-2H-pyridin-3-ylidene)-1,3-pentadienyl)-1-ethyl-6-hydroxy-4-methyl-2-oxo-1,2-dihydropyridine-3-carbonitrile.

31. The method as defined in claim 26, wherein said physiologically tolerated salt is selected from the group consisting of ammonium, sodium, potassium, N-methylmorpholinium, monoethanolammonium, diethanolammonium and triethanolammonium salts.

32. The method as defined in claim 26, wherein said colorant has a pH of from 2 to 11.

33. The method as defined in claim 26, wherein the reducing agent is an alkali metal sulfite, an alkali metal hydrogen sulfite, an alkali metal metabisulfite, an ammonium sulfite or an ammonium hydrogen sulfite.

34. The method as defined in claim 26, wherein the reducing agent is a combination of an alkali metal sulfite, an alkali metal hydrogen sulfite, an alkali metal metabisulfite, an ammonium sulfite or an ammonium hydrogen sulfite with at least one member selected from the group consisting of reductones and thiols.

35. The method as defined in claim 26, wherein the oxidant is a bleaching powder containing from 5 to 50 percent by weight of a persulfate compound selected from the group consisting of alkali metal persulfates and ammonium persulfates.

36. The method as defined in claim 26, wherein the oxidant is a hydrogen peroxide solution in combination with a bleaching powder containing from 5 to 50 percent by weight of a persulfate compound selected from the group consisting of alkali metal persulfates and ammonium persulfates.

37. A two component kit for coloring and later decolorizing hair, said kit consisting of a first component and a second component, said first component consisting of a hair colorant and said second component consisting of a decolorizing agent;

wherein said decolorizing agent is a reducing agent or an oxidant; and wherein said colorant comprises at least one monomethine or polymethine dye of tautomeric formula (Ia/Ib), or a physiologically tolerated salt thereof,

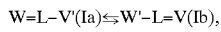

wherein W=L–V' and W'=L–V are tautomers, and said W and said V each, independently of each other, is a substituted five-member or six-member heterocyclic ring, so that said W and W' are the same and said V and V' are the same, except that said W and said V each have a —C(=C)— group and said W' and said V' each have a =C(OH)— group in place of said —C(=C)— group in said substituted five-member or six-member heterocyclic ring, and wherein said substituted five-member or six-member heterocyclic ring for said W and for said V is each, independently of each other, selected from the group consisting of substituted pyrazolones, substituted pyridones, substituted dioxothiazolines, substituted rhodanines, substituted dioxoimidazolidines and substituted barbituric acid; and wherein L represents a bridging group of formula

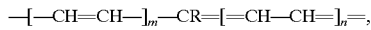

wherein R is hydrogen, a phenyl group, a halogen atom, a methyl group or a carboxamido group, and wherein m and n, independently of each other, are each 0, 1 or 2, with the proviso that n+m does not exceed 2.

38. The two-component kit as defined in claim 37, wherein said colorant includes a polymer selected from the group consisting of natural polymers, modified polymers of natural origin and synthetic polymers.

39. The two-component kit as defined in claim 37, wherein said polymethine dye is a trimethine unit or a pentamethine unit.

40. The two-component kit as defined in claim 37, wherein said at least one monomethine or polymethine dye is selected from the group consisting of dye compounds of the formulas (II) to (IV):

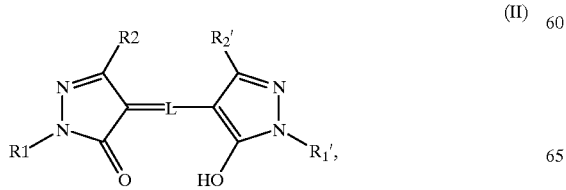

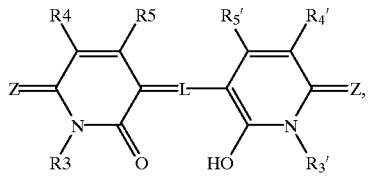

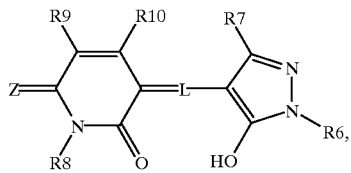

wherein R1, R1' and R6 denote hydrogen; a straight-chain or branched $C_1$- to $C_8$-alkyl group; a hydroxyethyl group; a dihydroxypropyl group; a methoxyethyl group; a carboxyethyl group; a $C_1$- to $C_4$-sulfoalkyl group; a phenyl group; a substituted phenyl group substituted with one or more halogen atoms, with one or two sulfonic acid groups, with one or two carboxyl groups, with one or more straight-chain or branched $C_1$- to $C_8$-alkyl groups or with one or more $C_1$- to $C_8$-alkoxy groups; a benzyl group; a substitute benzyl group substituted with one or more halogen atoms, a $C_1$- to $C_4$-alkyl group, a hydroxy group, a methoxy group, a carboxyl group, a nitro group or an amino group or a five-member or six-member saturated or unsaturated heterocyclic ring; wherein R1 and R1' are equal or different from each other; and wherein R2, R2' and R7 denote hydrogen; a branched or straight chain $C_1$- to $C_6$-alkyl group; a phenyl group; an acylated phenyl group; a sulfonylated phenyl group; an amino group; an acylated amino group; a sulfonylated amino group; an acetyl group; a methoxy group; a carboxyl group; a carboxyl group esterified with a straight-chain or branched $C_1$- to $C_8$-alcohol, with ethylene glycol monomethyl ether or with ethylene glycol monoethyl ether; a carboxamido group; a carboxanilido group; a 2-amino-2-oxyethyl group or a nitrilo group, R2 and R2' being equal or different, and wherein R3, R3' and R8 denote hydrogen; a straight-chain or branched $C_1$- to $C_{11}$-alkyl group; a straight-chain or branched $C_1$- to $C_{11}$-monohydroxyalkyl group; a straight-chain or branched $C_1$- to $C_{11}$-dihydroxyalkyl group; a straight-chain or branched $C_1$- to $C_{11}$-alkoxyalkyl group; a straight-chain or branched $C_1$- to $C_{11}$-monoalkylamino group; an amino group of formula $(CH_2)_x$—NR11R12 wherein x is an integer from 0 to 3 and R11 and R12, independently of each other, denote an $C_1$- to $C_3$-alkyl group, a $C_2$- to $C_4$-sulfoalkyl group, a $C_2$- to $C_8$-carboxyalkyl group; a phenyl group; a substituted phenyl group having one or more halogen atoms, one or two sulfonic acid groups, one or more carboxyl groups, one or more straight-chain or branched $C_1$- to $C_8$-alkyl groups or one or more straight-chain or branched $C_1$- to $C_8$-alkoxy groups; a benzyl group; a substituted benzyl group having one or more halogen atoms, one or more $C_1$- to to $C_4$-alkyl groups, a hydroxy group, a methoxy group, a nitro group or an amino group; a phenylethyl group; a five-member or six-member aromatic or nonaromatic heterocyclic group; a five-member or six-member aromatic or nonaromatic heterocyclic group attached by a methylene group; a pyrrolidino($C_1$- or $C_3$-)alkyl group; a morpholino($C_1$- or $C_3$-)alkyl group; a piperazino($C_1$- or $C_3$-)alkyl group; a piperidino($C_1$- or $C_3$-)alkyl group; a pyridino($C_1$- or $C_3$-)alkyl group or a trialkylammoniumalkyl group of formula R13—N(R14)$_3^+$ with R13 denoting a $C_1$- to $C_6$-alkylene group, R14 denoting a methyl or ethyl group and with a total number of carbon atoms being equal to 5 to 9, wherein R3 and R3' are equal or different from each other; and wherein R4, R4' and R9 denote hydrogen, a nitro group, a carboxylate ester group, a carboxamido group, a sulfonic acid group, a sulfomethyl group, a methanesulfonyl group, a pyridinium group or an imidazolium group, R4 and R4' being equal or different from each other; and wherein R5, R5' and R10 denote hydrogen, a $C_1$- to $C_4$-alkyl group, a $C_5$- to $C_6$-cycloalkyl group, a phenyl group, methoxyphenyl group, a benzyl group, a phenylethyl group or a carboxyl group, R5 and R5' being equal or different from each other, and wherein Z denotes an oxygen or a group of formula C(CN)$_2$, C(CN)COOQ or C(COOQ)$_2$, wherein Q denotes a $C_1$- to $C_8$-alkyl group or an ethylene glycol mono($C_3$ to $C_7$)alkyl ether group, and L denotes said bridging group of said formula —[—CH=CH—]$_m$—CR=[=CH—CH=]$_n$=, wherein said R is said hydrogen, said phenyl group, said methyl group or said carboxamido group, and wherein m and n, independently of each other, are each 0, 1 or 2, with the proviso that n+m does not exceed 2.

41. The two component kit as defined in claim 37, wherein said at least one monomethine or polymethine dye is selected from the group consisting of 4-(5-hydroxy-1,3-dimethyl-1H-pyrazol-4-ylmethylene)-2,5-dimethyl-2,4-dihydro-pyrazol-3-one,2-(2-hydroxyethyl)4-(5-hydroxy-1-(2-hydroxyethyl)-3-methyl-1H-pyrazol-4-ylmethylene)-5-methyl-2,4-dihydropyrazol-3-one; 4-(5-hydroxy-3-methyl-1-(4-sulfophenyl)-1H-pyrazol-4-ylmethylene)-5-methyl-2-(4-sulfo-phenyl)-2,4-dihydropyrazol-3-one; diammonium 4-(5-hydroxy-3-methyl-1-(4-sulfophenyl)-1H-pyrazol-4-ylmethylene)-5-methyl-2-(4-sulfophenyl)-2,4-dihydropyrazol-3-one; 4-(3-(5-hydroxy-1,3-dimethyl-1H-pyrazol-4-yl)allylidene)-2,5-dimethyl-2,4-dihydro-pyrazol-3-one; 5-amino-4-(3-(3-amino-5-hydroxy-1-phenyl-1H-pyrazol-4-yl)allylidene)-2-phenyl-2,4-dihydropyrazol-3-one, 2-(2-hydroxyethyl)-4-(3-(5-hydroxy-1-(2-hydroxyethyl)-3-methyl-1H-pyrazol-4-yl)allylidene)-5-methyl-2,4-dihydropyrazol-3-one; 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; disodium 4-(3-(5-hydroxy-3-methyl-1-(4-sulfophenyl)-1H-pyrazol-4-yl)allylidene)-5-methyl-2-(4-sulfophenyl)-2,4-dihydropyrazol-3-one; 4-(3-(5-hydroxy-3-methyl-1-(4-sulfophenyl)-1H-pyrazol-4-yl)-2-butenylidene)-5-methyl-2-(4-sulfophenyl)-2,4-dihydropyrazol-3-one; tripotassium 4-(3-(5-hydroxy-3-methyl-1-(4-sulfo-phenyl)-1H-pyrazol-4-yl)-2-butenylidene)-5-methyl-2-(4-sulfophenyl)-2,4-dihydropyrazol-3-one; 4-(3-(3-carboxy-5-oxo-1-(4-sulfophenyl)-1,5-dihydro-pyrazol-4-ylidene)propenyl)-5-hydroxy-1-(4-sulfophenyl)-1H-pyrazol-3-carboxylic acid; tetrasodium 4-(3-(3-carboxy-5-oxo-1-(4-sulfophenyl)-1,5-dihydropyrazol-4-ylidene)propenyl)-5-hydroxy-1-(4-sulfophenyl)-1H-pyrazol-3-carboxylic acid; 5-hydroxy-4-(3-(3-methoxycarbonyl-5-oxo-1-(4-sulfophenyl)-1,5-dihydropyrazol-4-ylidene)-propenyl)-1-(4-sulfophenyl)-1H-pyrazol-3-carboxylic acid methyl ester; 4-(5-(5-hydroxy-1,3-dimethyl-1H-pyrazol-4-yl)penta-2,4-dienylidene)-2,5-dimethyl-2,4-dihydropyrazol-3-one, 5-amino-4-(5-(3-amino-5-hydroxy-1-phenyl-1H-pyrazol-4-yl)penta-2,4-dienylidene)-2-phenyl-2,4-di-hydropyrazol-3-one; 2-(2-hydroxyethyl)-4-(5-(5-hydroxy-1-(2-hydroxyethyl)-3-methyl-1H-pyrazol-4-yl)penta-2,4-dienylidene)-5-methyl-2,4-dihydro-pyrazol-3-one; 4-(5-(5-hydroxy-3-methyl-1-(4-sulfophenyl)-1H-pyrazol-4-yl)-penta-2,4-dienylidene)-5-methyl-2-(4-sulfophenyl)-2,4-dihydropyrazol-3-one; dipotassium 4-(5-(5-hydroxy-3-methyl-1-(4-sulfophenyl)-1H-pyrazol-4-yl)penta-2,4-dienylidene)-5-methyl-2-(4-sulfophenyl)-2,4-dihydropyrazol-3-one; 4-(5-(3-carboxy-5-oxo-1-(4-sulfophenyl)-1,5-dihydropyrazol-4-ylidene)penta-1,3-dienyl)-5-hydroxy-1-(4-sulfophenyl)-1H-pyrazol-3-carboxylic acid; dipotassium 4-(5-(3-carboxy-5-oxo-1-(4-sulfo-phenyl))-1,5-dihydropyrazol-4-ylidene)-penta-1,3-dienyl)-5-hydroxy-1-(4-sulfo-phenyl)-1H-pyrazole-3-carboxylic acid; 6-hydroxy-1-(2-hydroxyethyl)-5-(3-(1-(2-hydroxyethyl)-3-methyl-5-oxo-1,5-dihydropyrazol-4-ylidene)-propenyl)-4-methyl-2-oxo-1,2-dihydropyridine-3-carbonitrile; 6-hydroxy-5-(3-(1-(2-hydroxyethyl-3-methyl-5-oxo-1,5-dihydro-pyrazol-4-ylidene)propenyl)-4-methyl-2-oxo-1-(4-sulfophenyl)-1,2-dihydro-pyridine-3-carbonitrile; potassium 6-hydroxy-5-(3-(1-(2-hydroxyethyl)-3-methyl-5-oxo-1,5-dihydropyrazol-4-ylidene)propenyl-4-methyl-2-oxo-1-(4-sulfophenyl)-1,2-dihydropyridine-3-carbonitrile; 6-hydroxy-4-methyl-5-(3-(3-methyl-5-oxo-1-(4-sulfophenyl)-1,5-dihydropyrazol-4-ylidene)propenyl)-2-oxo-1-(4-sulfophenyl)-1,2-dihydropyridine-3-carbonitrile; dipotassium 6-hydroxy-4-methyl-5-(3-(3-methyl-5-oxo-1-(4-sulfophenyl)-1,5-dihydropyrazol-4-yl idene)-propenyl-2-oxo-1-(4-sulfophenyl)-1,2-dihydropyridine-3-carbonitrile; 6-hydroxy4-methyl-5-(3-(3-methyl-5-oxo-1-phenyl-1,5-dihydropyrazole-4-ylidene)-propenyl)-2-oxo-1-(3-sulfophenyl)-1,2-dihydropyridine-3-carbonitrile; 4-(3-(5-cyano-2-hydroxy-4-methyl-6-oxo-1-phenyl-1,6-dihydropyridin-3-yl)allylidene)-5-oxo-1-(4-sulfophenyl)-4,5-dihydro-1H-pyrazole-3-carboxylic acid; 6-hydroxy-5-(3-(1-(2-hydroxyethyl)-3-methyl-5-oxo-1,5-dihydropyrazol-4-ylidene)propenyl)-4-methyl-2-oxo-1-phenyl-1,2-dihydropyridine-3-carbonitrile; 5-(3-(4-carboxy-2,6-dioxo-1,6-dihydro-2H-pyridin-3-ylidene)propenyl)-6-hydroxy-2-oxo-1,2-dihydro-pyridine-4-carboxylic acid; 2-(3-cyano-5-(3-(5-cyano-6-dicyanomethylene-4-methyl-2-oxo-1,6-dihydro-2H-pyridin-3-ylidene)propenyl)4-hydroxy-4-methyl-1H-pyridin-2-ylidene)-malononitrile; 5-(3-(5-cyano-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carbonitrile; triethylammonium-5-(3-(5-cyano-1-ethyl-4-methyl-2,6-dioxo-1,6-dihydro-2H-pyridin-3-ylidene)propenyl-1-ethyl-6-hydroxy-4-methyl-2-oxo-1,2-dihydropyridine-3-carbonitrile; 5-(3-(5-cyano-1-(2-hydroxyethyl)4-methyl-2,6-dioxo-1,6-dihydro-2H-pyridin-3-ylidene)propenyl)-6-hydroxy-1-(2-hydroxyethyl)-4-methyl-2-oxo-1,2-dihydropyridine-3-carbonitrile; 5-(3-(5-cyano-1-ethyl-4-(4-methoxyphenyl)-2,6-dioxo-1,6-dihydro-2H-pyridin-3-ylidene)propenyl)-1-ethyl-6-hydroxy-4-(4-methoxyphenyl)-2-oxo-1,2-dihydro-pyridine-3-carbonitrile; 1-butyl-5-(3-(1-butyl-5-cyano-4-methyl-2,6-dioxo-1,6-dihydro-2H-pyridin-3-ylidene)propenyl)-6-hydroxy-4-methyl-2-oxo-1,2-dihydro-pyridine-3-carbonitrile; 5-(3-(5-cyano-1-(3-methoxypropyl)-4-methyl-2,6-dioxo-1,6-dihydro-2H-pyridin-3-ylidene)propenyl)-6-hydroxy-1-(3-methoxypropyl)-4-methyl-2-oxo-1,2-dihydropyridine-3-carbonitrile; 5-(3-(5-cyano-1-cyclohexyl-4-methyl-2,6- dioxo-1,6-dihydro-2H-pyridin-3-ylidene)propenyl)-1-ethyl-6-hydroxy-4-methyl-2-oxo-1,2-dihydropyridine-3-carbonitrile; 5-(3-(5-cyano-4-methyl-1-(2-morpholin-4-ylethyl)-2,6-dioxo-1,6-dihydro-2H-pyridin-3-ylidene)propenyl)-6-hydroxy-4-methyl-1-(2-morpholin-4-ylethyl)-2-oxo-1,2-dihydro-pyridine-3-carbonitrile; 5-(3-(5-cyano-4-methyl-2,6-dioxo-1-(4-sulfophenyl)-1,6-dihydro-2H-pyridin-3-ylidene)propenyl)-6-hydroxy-4-methyl-2-oxo-1-(4-sulfo-phenyl)-1,2-dihydropyridine-3-carbonitrile; 5-(3-(5-cyano-4-methyl-2,6-dioxo-1-(3-sulfophenyl)-1,6-dihydro-2H-pyridin-3-ylidene)propenyl)-6-hydroxy-4-methyl-2-oxo-1-(3-sulfophenyl)-1,2-dihydropyridine-3-carbonitrile; 5-(3-(5-cyano-1-dimethylamino-4-methyl-2,6-dioxo-1,6-dihydro-2H-pyridin-3-ylidene)propenyl)-1-dimethylamino-6-hydroxy-4-methyl-2-oxo-1,2-dihydropyridine-3-carbonitrile; 5-(3-(5-carbamoyl-1-ethyl-4-methyl-2,6-dioxo-1,6-dihydro-2H-pyridin-3-ylidene)propenyl)-1-ethyl-6-hydroxy-4-methyl-2-oxo-1,2-dihydropyridine-3-carboxamide, 1-ethyl-3-(3-(1-ethyl-2-hydroxy-5-methane-sulfonyl-4-methyl-6-oxo-1,6-dihydropyridin-3-yl)allylidene)-5-methanesulfonyl-4-methyl-3H-pyridino-2,6-dione and 5-(5-(5-cyano-1-ethyl-4-methyl-2,6-dioxo-1, 6-dihydro-2H-pyridin-3-ylidene)-1,3-pentadienyl)-1-ethyl-6-hydroxy-4-methyl-2-oxo-1,2-dihydropyridine-3-carbonitrile.

42. The two-component kit as defined in claim 37, wherein said physiologically tolerated salt is selected from the group consisting of ammonium, sodium, potassium, N-methylmorpholinium, monoethanol-ammonium, diethanolammonium and triethanolammonium salts.

43. The two-component kit as defined in claim 37, wherein said colorant has a pH of from 2 to 11.

44. The two-component kit as defined in claim 37, wherein the reducing agent is an alkali metal sulfite, an alkali metal hydrogen sulfite, an alkali metal metabisulfite, an ammonium sulfite or an ammonium hydrogen sulfite.

45. The two-component kit as defined in claim 37, wherein the reducing agent is a combination of an alkali metal sulfite, an alkali metal hydrogen sulfite, an alkali metal metabisulfite, an ammonium sulfite or an ammonium hydrogen sulfite with at least one member selected from the group consisting of reductones and thiols.

46. The two-component kit as defined in claim 37, wherein the oxidant is a bleaching powder containing from 5 to 50 percent by weight of a persulfate compound selected from the group consisting of alkali metal persulfates and ammonium persulfates.

47. The two-component kit as defined in claim 37, wherein the oxidant is a hydrogen peroxide solution in combination with a bleaching powder containing from 5 to 50 percent by weight of a persulfate compound selected from the group consisting of alkali metal persulfates and ammonium persulfates.

* * * * *